United States Patent
Policker et al.

(10) Patent No.: US 7,437,195 B2
(45) Date of Patent: *Oct. 14, 2008

(54) REGULATION OF EATING HABITS

(75) Inventors: Shai Policker, Moshav zur Moshe (IL);
Ricardo Aviv, Haifa (IL); Ophir Bitton, Zichron Yaakov (IL)

(73) Assignee: Metalure N.V., Curacao (AN)

( * ) Notice: Subject to any disclaimer, the term of this patent is extended or adjusted under 35 U.S.C. 154(b) by 324 days.

This patent is subject to a terminal disclaimer.

(21) Appl. No.: 10/250,714

(22) PCT Filed: Jan. 3, 2002

(86) PCT No.: PCT/IL02/00007

§ 371 (c)(1),
(2), (4) Date: Oct. 14, 2003

(87) PCT Pub. No.: WO02/053093

PCT Pub. Date: Jul. 11, 2002

(65) Prior Publication Data

US 2004/0059393 A1     Mar. 25, 2004

Related U.S. Application Data

(60) Provisional application No. 60/259,925, filed on Jan. 5, 2001.

(51) Int. Cl.
*A61N 1/00* (2006.01)
(52) U.S. Cl. ........................................ 607/40
(58) Field of Classification Search ............... 607/40, 607/45, 58
See application file for complete search history.

(56) References Cited

U.S. PATENT DOCUMENTS 3,411,507 A     11/1968     Wingrove (Continued)

FOREIGN PATENT DOCUMENTS

EP     0 057 048     8/1982

(Continued)

OTHER PUBLICATIONS

William L. Hasler, The Physiology of Gastic Motility and Gastric Emptying, Textbook of Gastroenterology, Third Edition, Edited by Yamada, pp. 188-207.*

(Continued)

*Primary Examiner*—George R. Evanisko
*Assistant Examiner*—Rex Holmes
(74) *Attorney, Agent, or Firm*—Wolf, Block, Schorr & Solis-Cohen LLP; William H. Dippert

(57) ABSTRACT

A method for treating a subject is provided, including receiving a sensor signal responsive to the subject eating, analyzing the sensor signal, and driving a current into tissue of the subject responsive to analyzing the signal. The current is typically driven into muscle tissue of the subject's stomach (20). Preferably, receiving the sensor signal includes sensing electrical potential change generated responsive to contraction of a muscle such as a stomach muscle of the subject. In a preferred embodiment, the sensor signal is analyzed with respect to the timing of ingestion, and a level of compliance of the subject with a desired ingestion schedule is determined. As appropriate, a parameter of the current driven into the tissue may be configured such that the application of the current to the tissue induces in the subject a sensation of satiation, discomfort, nausea, or vertigo.

73 Claims, 12 Drawing Sheets

U.S. PATENT DOCUMENTS

| | | | |
|---|---|---|---|
| 3,516,412 | A | 6/1970 | Ackerman |
| 3,737,579 | A | 6/1973 | Bolduc |
| 4,000,745 | A | 1/1977 | Goldberg et al. |
| 4,010,758 | A | 3/1977 | Rockland et al. |
| 4,133,315 | A | 1/1979 | Berman et al. |
| 4,177,818 | A | 12/1979 | De Pedro |
| 4,235,246 | A | 11/1980 | Weiss |
| 4,280,503 | A | 7/1981 | Ackerman |
| 4,313,448 | A | 2/1982 | Stokes |
| 4,357,946 | A | 11/1982 | Dutcher et al. |
| 4,378,023 | A | 3/1983 | Trabucco |
| 4,416,267 | A | 11/1983 | Garren et al. |
| 4,452,254 | A | 6/1984 | Goldberg et al. |
| 4,485,805 | A | 12/1984 | Foster, Jr. |
| 4,592,339 | A | 6/1986 | Kuzmak |
| 4,823,808 | A | 4/1989 | Clegg et al. |
| 4,975,682 | A | 12/1990 | Kerr et al. |
| 5,074,868 | A | 12/1991 | Kuzmak |
| 5,101,814 | A | 4/1992 | Palti |
| 5,103,804 | A | 4/1992 | Abele et al. |
| 5,105,812 | A | 4/1992 | Corman |
| 5,188,104 | A | 2/1993 | Wernicke |
| 5,226,429 | A | 7/1993 | Kuzmak |
| 5,234,454 | A | 8/1993 | Bangs |
| 5,247,938 | A | 9/1993 | Silverstein et al. |
| 5,263,480 | A | 11/1993 | Wernicke et al. |
| 5,368,028 | A | 11/1994 | Palti |
| 5,423,872 | A | 6/1995 | Cigaina |
| 5,449,368 | A | 9/1995 | Kuzmak |
| 5,514,175 | A * | 5/1996 | Kim et al. .................. 607/136 |
| 5,540,730 | A | 7/1996 | Terry et al. |
| 5,551,425 | A | 9/1996 | Essen-Moller |
| 5,601,604 | A | 2/1997 | Vincent |
| 5,690,691 | A | 11/1997 | Chen |
| 5,704,368 | A | 1/1998 | Asano et al. |
| 5,716,385 | A | 2/1998 | Mittal et al. |
| 5,792,210 | A * | 8/1998 | Wamubu et al. ............... 607/58 |
| 5,795,304 | A | 8/1998 | Sun et al. |
| 5,836,994 | A | 11/1998 | Bourgeois |
| 5,837,006 | A | 11/1998 | Ocel et al. |
| 5,861,014 | A | 1/1999 | Familoni |
| 5,868,141 | A | 2/1999 | Ellias |
| 5,938,669 | A | 8/1999 | Klaiber et al. |
| 5,979,449 | A | 11/1999 | Steer |
| 5,991,649 | A | 11/1999 | Garfield et al. |
| 5,995,872 | A | 11/1999 | Bourgeois |
| 6,026,326 | A | 2/2000 | Bardy |
| 6,041,258 | A | 3/2000 | Cigaina et al. |
| 6,067,991 | A | 5/2000 | Forsell |
| 6,083,249 | A | 7/2000 | Familoni |
| 6,091,992 | A | 7/2000 | Bourgeois |
| 6,092,528 | A | 7/2000 | Edwards |
| 6,104,955 | A | 8/2000 | Bourgeois |
| 6,115,635 | A | 9/2000 | Bourgeois |
| 6,129,685 | A | 10/2000 | Howard |
| 6,132,372 | A | 10/2000 | Essen-Moller |
| 6,135,987 | A | 10/2000 | Tsai et al. |
| 6,216,045 | B1 | 4/2001 | Black et al. |
| 6,243,607 | B1 | 6/2001 | Mintchev et al. |
| 6,249,697 | B1 | 6/2001 | Asano et al. |
| 6,334,073 | B1 * | 12/2001 | Levine ........................ 607/58 |
| 6,363,937 | B1 | 4/2002 | Hovda et al. |
| 6,381,495 | B1 | 4/2002 | Jenkins |
| 6,405,732 | B1 | 6/2002 | Edwards |
| 6,411,842 | B1 | 6/2002 | Cigaina et al. |
| 6,415,178 | B1 | 7/2002 | Ben-Haim et al. |
| 6,427,089 | B1 | 7/2002 | Knowlton |
| 6,449,511 | B1 | 9/2002 | Mintchev et al. |
| 6,454,699 | B1 | 9/2002 | Forsell |
| 6,535,764 | B2 | 3/2003 | Imran et al. |
| 6,571,127 | B1 | 5/2003 | Ben-Haim et al. |
| 6,572,542 | B1 | 6/2003 | Houben et al. |
| 6,584,348 | B2 | 6/2003 | Glukhovsky |
| 6,591,137 | B1 * | 7/2003 | Fischell et al. ................ 607/40 |
| 6,600,953 | B2 | 7/2003 | Flesler et al. |
| 6,606,523 | B1 | 8/2003 | Jenkins |
| 6,609,025 | B2 * | 8/2003 | Barrett et al. .................. 607/2 |
| 6,612,983 | B1 | 9/2003 | Marchal |
| 6,652,444 | B1 | 11/2003 | Ross |
| 6,658,297 | B2 | 12/2003 | Loeb |
| 6,684,104 | B2 | 1/2004 | Gordon |
| 6,735,477 | B2 * | 5/2004 | Levine ........................ 607/58 |
| 6,745,079 | B2 | 6/2004 | King |
| 6,754,536 | B2 | 6/2004 | Swoyer et al. |
| 6,826,428 | B1 | 11/2004 | Chen et al. |
| 6,832,114 | B1 | 12/2004 | Whitehurst |
| 6,852,110 | B2 | 2/2005 | Roy et al. |
| 6,853,862 | B1 | 2/2005 | Marchal et al. |
| 6,869,431 | B2 | 3/2005 | Maguire et al. |
| 6,876,885 | B2 | 4/2005 | Swoyer et al. |
| 6,895,279 | B2 | 5/2005 | Loeb et al. |
| 6,918,906 | B2 | 7/2005 | Long |
| 6,939,349 | B2 | 9/2005 | Fleischman et al. |
| 6,947,792 | B2 | 9/2005 | Ben-Haim et al. |
| 6,952,613 | B2 | 10/2005 | Swoyer et al. |
| 7,043,295 | B2 | 5/2006 | Starkebaum |
| 7,054,690 | B2 | 5/2006 | Imran |
| 7,076,305 | B2 | 7/2006 | Imran et al. |
| 7,076,306 | B2 | 7/2006 | Marchal et al. |
| 2001/0011543 | A1 | 8/2001 | Forsell |
| 2002/0026141 | A1 | 2/2002 | Houben |
| 2002/0103424 | A1 | 8/2002 | Swoyer et al. |
| 2003/0009202 | A1 | 1/2003 | Levine |
| 2003/0045919 | A1 | 3/2003 | Swoyer et al. |
| 2003/0055464 | A1 | 3/2003 | Darvish |
| 2003/0066536 | A1 | 4/2003 | Forsell |
| 2003/0144708 | A1 | 7/2003 | Starkebaum |
| 2003/0195600 | A1 | 10/2003 | Tronnes et al. |
| 2003/0208212 | A1 | 11/2003 | Cigaina |
| 2003/0208242 | A1 | 11/2003 | Harel et al. |
| 2003/0220678 | A1 | 11/2003 | Tronnes et al. |
| 2004/0044376 | A1 | 3/2004 | Flesler et al. |
| 2004/0059393 | A1 | 3/2004 | Policker et al. |
| 2004/0088023 | A1 | 5/2004 | Imran et al. |
| 2004/0107004 | A1 | 6/2004 | Levine et al. |
| 2004/0147816 | A1 * | 7/2004 | Policker et al. ............. 600/300 |
| 2004/0158138 | A1 | 8/2004 | Kilcoyne et al. |
| 2004/0162469 | A1 | 8/2004 | Imran |
| 2004/0162595 | A1 * | 8/2004 | Foley ........................ 607/40 |
| 2004/0167583 | A1 | 8/2004 | Knudson et al. |
| 2004/0193184 | A1 | 9/2004 | Laufer et al. |
| 2004/0236316 | A1 | 11/2004 | Danitz et al. |
| 2004/0249421 | A1 | 12/2004 | Harel et al. |
| 2005/0021101 | A1 | 1/2005 | Chen et al. |
| 2005/0055038 | A1 | 3/2005 | Kelleher et al. |
| 2005/0065505 | A1 | 3/2005 | Ryan |
| 2005/0075654 | A1 | 4/2005 | Kelleher |
| 2005/0090873 | A1 | 4/2005 | Imran |
| 2005/0107829 | A1 | 5/2005 | Edwards et al. |
| 2005/0143784 | A1 | 6/2005 | Imran |
| 2005/0183732 | A1 | 8/2005 | Edwards |
| 2005/0192615 | A1 | 9/2005 | Torre et al. |
| 2005/0203500 | A1 | 9/2005 | Saadat et al. |
| 2005/0209653 | A1 | 9/2005 | Herbert et al. |
| 2005/0222638 | A1 | 10/2005 | Foley et al. |
| 2006/0142803 | A1 | 6/2006 | Mintchev |
| 2006/0173238 | A1 | 8/2006 | Starkebaum |
| 2006/0247718 | A1 | 11/2006 | Starkebaum |

FOREIGN PATENT DOCUMENTS

| | | |
|---|---|---|
| EP | 0 129 483 | 12/1984 |
| JP | EP 144705 | 10/1984 |
| JP | 2003319945 | 11/2003 |

| | | |
|---|---|---|
| US | EP 1 447 052 | 8/2004 |
| WO | WO 94/01172 | 1/1994 |
| WO | WO 97/25098 | 7/1997 |
| WO | WO 98/10830 | 3/1998 |
| WO | WO 99/03533 | 1/1999 |
| WO | WO 01/41671 | 6/2001 |
| WO | WO 02/26101 | 4/2002 |
| WO | WO 02/053093 | 7/2002 |
| WO | WO 02/082968 | 10/2002 |
| WO | WO 02/089655 | 11/2002 |
| WO | WO 03/020365 | 3/2003 |
| WO | WO 2004/043280 | 5/2004 |
| WO | WO 2004/066903 | 8/2004 |
| WO | WO 2004/069330 | 8/2004 |
| WO | WO 2004/091361 | 10/2004 |
| WO | WO 2004/096337 | 11/2004 |
| WO | WO 2004/112563 | 12/2004 |
| WO | WO 2005/007232 | 1/2005 |
| WO | WO 2005/007237 | 1/2005 |
| WO | WO 2005/009288 | 2/2005 |
| WO | WO 2005/016181 | 2/2005 |
| WO | WO 2005/023081 | 3/2005 |
| WO | WO 2005/037152 | 4/2005 |
| WO | WO 2005/041749 | 5/2005 |
| WO | WO 2005/087310 | 9/2005 |
| WO | WO 2006/035446 | 4/2006 |
| WO | WO 2006/118790 | 11/2006 |

OTHER PUBLICATIONS

U.S. Appl. No. 10/237,263.
Meda et al., Quarterly J. Exper. Physiol. 69:719-735 (1984).
Eddiestone et al., J. Membrane Biol. 77:1-141 (1984).
A book entitled, Textbook of Gastroenterology, 3$^{rd}$ edition, edited by Yamada (Lippincott, Williams & Wilkins), Chapter 10.
An abstract entitled. "Gastric myoelectrical pacing as therapy for morbid obesity: Preliminary results," by Cigaina et al., retrieved on Dec. 24, 2000 from the Web-site http://www.med-online.com/transneuronix/Product/abstract.htm.
An abstract entitled, "Implantable gastric stimulator (IGS) as therapy for morbid obesity: Equipment, surgical technique and stimulation parameters", by Cigaina et al., retrieved on Dec. 24, 2000 from the Web-site http://www.med-online.com/.
M D Robertson, et al, "The influence of the colon on postprandial glucagons-like peptide 1 (7-36) amide concentration in man", Journal of Endocrinology (1999) 161, 25-31.
J. Schirra, et al, "Mechanisms of the antidiabetic action of subcutaneous glucagons-like peptide-1 (7-36) amide in non-insulin dependent diabetes mellitus", Journal of Endocrinology (1998) 156, 177-186.
T Vilsboll and Associates, Research design and methods, Diabetes, vol. 50, Mar. 2001, pp. 610-613.
Jeannie F. Todd, et al, "Subcutaneous glucagons-like peptide-1 improves postprandial glycaemic control over 3-week period in patients with early type 2 diabetes", Clinical Science (1998) 95, 325-329.
Daniel J. Drucker, "Development of glucagon-like peptide-1-based pharmaceuticals as therapeutic agents for the treatment of diabetes", Current Pharmaceutical Design, 2001, 7, 1399-1412.
Yamada, "Effects of drugs on electromechanical activities of the stomach and duodenum of conscious dogs", Nippon Heikatsukin Gakkai Zasshi. Feb. 1983;19(1):25-35. (abstract only).
Shemerovskii KA, "Effect of feeding on the activity of duodenal smooth muscle in dogs", Biull Eksp Biol Med. Oct. 1978;86(10):394-7. (Abstract only).

* cited by examiner

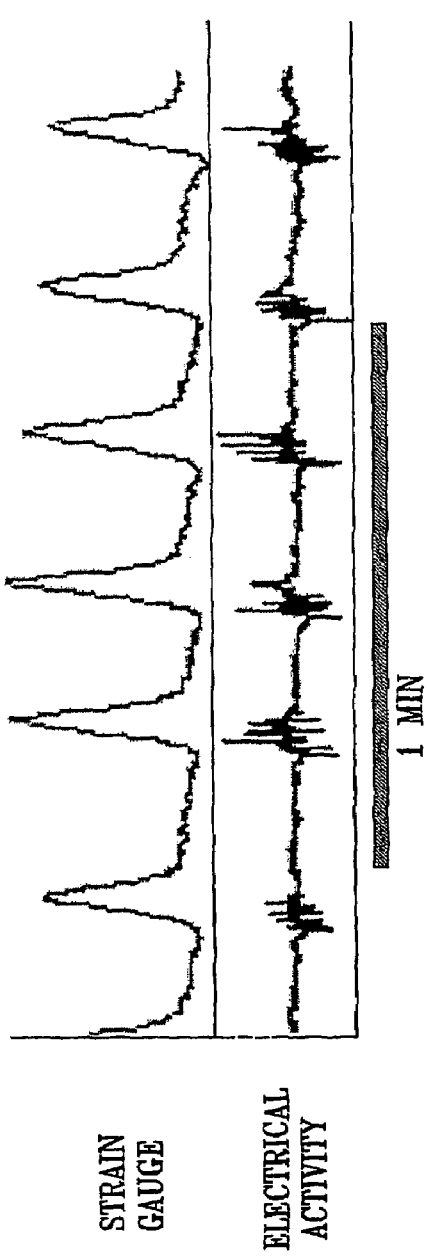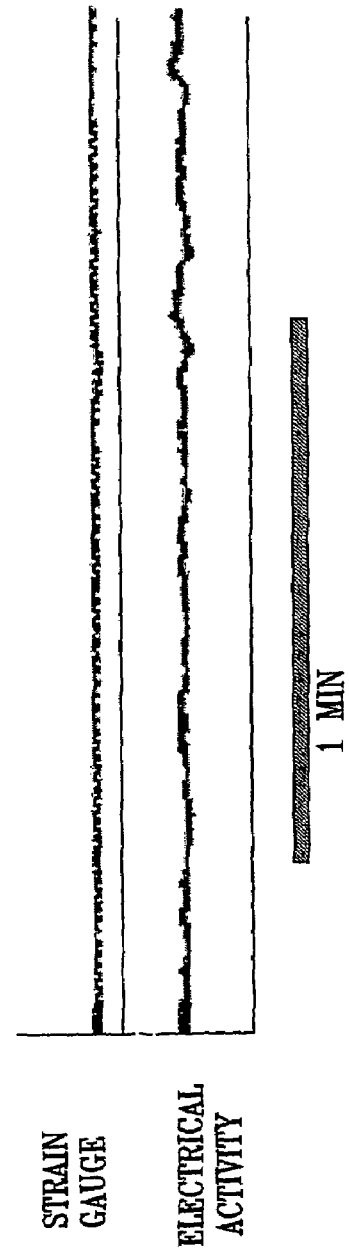
FIG. 9
FIG. 10

REGULATION OF EATING HABITS

This application is a U.S. National Phase filing of PCT Patent Application No. PCT/IL02/00007, filed Jan. 3, 2002, which is based upon U.S. Provisional Patent Application Ser. No. 60/259,925, filed Jan. 5, 2001, each of which is incorporated herewith by reference.

FIELD OF THE INVENTION

The present invention relates generally to appetite regulation, and specifically to invasive techniques and apparatus for appetite control and treating obesity.

BACKGROUND OF THE INVENTION

Morbid obesity is a difficult to treat chronic condition defined by a body mass index (BMI=mass/height$^2$[kg/m$^2$]) greater than 40. For obese persons, excessive weight is commonly associated with increased risk of cardiovascular disease, diabetes, degenerative arthritis, endocrine and pulmonary abnormalities, gallbladder disease and hypertension. Additionally, such persons are highly likely to experience psychological difficulties because of lifestyle restrictions such as reduced mobility and physical capacity, due to back pain, joint problems, and shortness of breath. In severe cases, this can contribute to absenteeism and unemployment. Moreover, impairment of body image can lead to significant psychological disturbances. Repeated failures of dieting and exercise to resolve the problem of obesity can result in feelings of despair and the development of clinical depression.

Bariatric surgery is often recommended for persons suffering from morbid obesity. Preferably, the invasive treatment is accompanied by changes in lifestyle, such as improved regulation of eating habits and an appropriate exercise regimen. Such lifestyle changes are dependent upon the self-discipline and cooperation of the patient.

A book entitled, *Textbook of Gastroenterology*, 3rd edition, edited by Yamada (Lippincott, Williams & Wilkns), which is incorporated herein by reference, has in Chapter 10 thereof, a description of the physiology of gastric motility and gastric emptying.

An abstract entitled, "Gastric myoelectrical pacing as therapy for morbid obesity: Preliminary results," by Cigaina et al., retrieved on Dec. 24, 2000 from the Web-site http://www.med-online.com/transneuronix/Product/abstract.htm, which is incorporated herein by reference, describes a method for applying monopolar and bipolar gastric stimulation to achieve weight loss.

An abstract entitled, "Implantable gastric stimulator (IGS) as therapy for morbid obesity: Equipment, surgical technique and stimulation parameters," by Cigaina et al., retrieved on Dec. 24, 2000 from the Web-site http://www.med-online.com/transneuronix/Product/abstract.htm, which is incorporated herein by reference, describes techniques of electrical signal therapy designed to treat obesity.

U.S. Pat. No. 6,129,685 to Howard, which is incorporated herein by reference, describes apparatus and methods for regulating appetite by electrical stimulation of the hypothalamus and by microinfusion of an appropriate quantity of a suitable drug to a distinct site or region within the hypothalamus.

U.S. Pat. No. 4,823,808 to Clegg et al., which is incorporated herein by reference, describes a method for treating obesity, including receiving a physiological measurement and generating audio and/or visual feedback for the patient to hear and/or see. The feedback is used for purposes of teaching behavior modification.

U.S. Pat. No. 5,868,141 to Ellias, which is incorporated herein by reference, describes an endoscopic stomach insert for reducing a patient's desire to eat.

U.S. Pat. No. 6,067,991 to Forsell, U.S. Pat. No. 5,601,604 to Vincent, U.S. Pat. No. 5,234,454 to Bangs, U.S. Pat. No. 4,133,315 to Berman et al., U.S. Pat. No. 4,416,267 to Garren et al., and U.S. Pat. Nos. 4,592,339, 5,449,368, 5,226,429 and 5,074,868 to Kuzmak, which are incorporated herein by reference, describe mechanical instruments for implantation in or around the stomach of an obese patient.

U.S. Pat. No. 5,690,691 to Chen et al., which is incorporated herein by reference, describes a gastric pacemaker for treating obesity and other disorders. The pacemaker includes multiple electrodes which are placed at various positions on the gastrointestinal (GI) tract, and deliver phased electrical stimulation to pace peristaltic movement of material through the GI tract.

U.S. Pat. No. 5,423,872 to Cigaina, which is incorporated herein by reference, describes apparatus for applying electrical pulses to the distal gastric antrum of a patient, so as to reduce the motility of the stomach and to thereby treat obesity or another disorder.

U.S. Pat. Nos. 5,188,104 and 5,263,480 to Wernicke et al., which are incorporated herein by reference, describe a method for stimulating the vagus nerve of a patient so as to alleviate an eating disorder.

U.S. Pat. Nos. 6,104,955, 6,091,992, and 5,836,994 to Bourgeois, U.S. Pat. No. 6,026,326 to Bardy, and U.S. Pat. No. 3,411,507 to Wingrove, which are incorporated herein by reference, describe the application of electrical signals to the GI tract to treat various physiological disorders.

U.S. Pat. No. 5,979,449 to Steer, which is incorporated herein by reference, describes an oral appliance for appetite suppression.

U.S. Pat. No. 4,975,682 to Kerr et al., which is incorporated herein by reference, describes apparatus for food intake regulation which is external to the body and which is based upon the voluntary cooperation of the subject in order to be effective.

U.S. Pat. Nos. 5,861,014, 5,716,385 and 5,995,872 are incorporated herein by reference, and describe methods and apparatus for stimulation of tissue, particularly gastrointestinal tract tissue.

PCT Patent Publication WO 98/10830 to Ben-Haim et al., entitled, "Fencing of cardiac muscles," and U.S. patent application Ser. No. 09/254,903 in the national phase thereof, both of which are assigned to the assignee of the present patent application and are incorporated herein by reference, describe various methods for controlling the behavior of muscle tissue, for example by blocking or altering the transmission of signals therethrough.

PCT Patent Publication WO 99/03533 to Ben-Haim et al., entitled, "Smooth muscle controller," and U.S. patent application Ser. No. 09/481,253 in the national phase thereof, both of which are assigned to the assignee of the present patent application and are incorporated herein by reference, describe apparatus and methods for applying signals to smooth muscle so as to modify the behavior thereof. In particular, apparatus for controlling the stomach is described in which a controller applies an electrical field to electrodes on the stomach wall so as to modify the reaction of muscle tissue therein to an activation signal, while not generating a propagating action potential in the tissue. In the context of the present patent application and in the claims, the use of such a non-excitatory signal to modify the response of one or more cells to electrical activation thereof, without inducing action potentials in the cells, is referred to as Excitable-Tissue Control (ETC). Use of an ETC signal is described with respect to treating obesity, by applying the ETC signal to the stomach so as to delay or prevent emptying of the stomach. In addition, a method is described for increasing the motility of the gastrointestinal tract, by applying an ETC signal to a portion of the tract in order to increase the contraction force generated in the portion and the stretching of nearby tissue.

SUMMARY OF THE INVENTION

It is an object of some aspects of the present invention to provide apparatus and methods for regulation of appetite and food ingestion.

It is a further object of some aspects of the present invention to provide improved apparatus and methods for treating obesity.

It is yet a further object of some aspects of the present invention to provide apparatus and methods that enable change in food ingestion habits in a predictable and controlled manner.

It is still a further object of some aspects of the present invention to provide apparatus and methods for bariatric surgery which are less drastic than those currently employed.

In preferred embodiments of the present invention, apparatus for regulating a patient's food ingestion comprises a sensor which detects: (a) the patient swallowing, (b) the filling of the patient's stomach, and/or (c) the onset of contractions in the stomach as a result of eating. Preferably, a timing module stores in an electronic memory the time of each swallow and/or meal. Additionally or alternatively, a measuring module stores in the memory the amount of food consumed in the meal. Further additionally or alternatively, the measuring module determines a quality of the food, for example whether it is predominantly solid or liquid. For most applications, a specific schedule of allowed food ingestion is pre-programmed by a physician into the memory, and a processor is continuously operative to detect whether food consumption is taking place in accordance with the programmed schedule. For some patients, the schedule may be less strict with respect to the drinking of liquids, and more strict with respect to the eating of solid food. When an exception from the schedule is detected, the processor actuates a signal generator to convey an ingestion-control signal to the patient, in order to encourage the patient to adhere to the schedule.

Typically, the ingestion-control signal is delivered to the patient's stomach via a set of electrodes placed in a vicinity thereof, so as to induce a sensation of satiety, discomfort, or minor nausea Thus, for example, in response to detecting a violation of the patient's prescribed diet and/or eating schedule, the processor may drive the signal generator to induce an unpleasant sensation (e.g., nausea) by altering the natural electrical activity of the stomach, thereby inducing gastric dysrhythmia. For some applications, the signal is applied to another site on or in the patient's body. For example, the ingestion-control signal may be applied mechanically or electrically in a vicinity of the cochlear nerve, so as to induce vertigo. Alternatively or additionally, the signal is applied so as to generate a brief pain sensation anywhere on the patient's body, which only recurs if the patient continues to eat.

Preferably, but not necessarily, the measuring module determines the quality of the food (e.g., solid or liquid) by interpreting electrical signals generated in the gastrointestinal tract. Further preferably, the measuring module makes the determination using techniques described in the above-cited *Textbook of Gastroenterology*, Volume II, Chapter 10, which is incorporated herein by reference. Alternatively or additionally, the determination may be made using chemical means (e.g., a pH sensor) or mechanical sensors.

For some applications, a signal is applied to the esophagus or to the lower esophageal sphincter, so as to cause contraction of muscle tissue therein, thereby making any further eating difficult or uncomfortable.

Alternatively or additionally, the ingestion-control signal is configured so as to induce a feeling of satiation, preferably but not necessarily using methods or apparatus described in U.S. patent application Ser. No. 09/734,358, entitled, "Acute and chronic electrical signal therapy for obesity," filed Dec. 11, 2000, or in U.S. Provisional Patent Application No. 60/259,925, entitled, "Regulation of eating habits," filed Jan. 5, 2001, both of which are assigned to the assignee of the present patent application and incorporated herein by reference. For example, methods described in those applications for engendering a feeling of satiation may be applied in conjunction with embodiments of the present invention, such that muscles in the vicinity of stretch receptors in the stomach are caused to contract, thereby resulting in decreased hunger sensations. Alternatively or additionally, the feeling of satiation is induced by applying electrical signals which enhance the mobility of chyme from the fundus to the antru=of the stomach, where stretch-receptor signals are generally generated to a greater extent for a given quantity of food than in the fundus.

Preferably, the schedule of allowed food ingestion can be modified after implantation of the apparatus, typically by means of a wireless communications link. In this manner, the schedule can be adjusted in response to changes in the patient's eating habits and experience with the apparatus.

There is therefore provided, in accordance with a preferred embodiment of the present invention, a method for treating a subject, including:

receiving a sensor signal responsive to the subject eating;
analyzing the sensor signal; and
driving a current into tissue of the subject responsive to analyzing the signal.

Typically, receiving the sensor signal includes sensing an electrical potential change generated responsive to contraction of a muscle of the subject. In addition, analyzing the sensor signal may include identifying a change in a measure of electrical impedance between two sites of the muscle. Alternatively or additionally, analyzing the sensor signal may include identifying a change in a frequency component of the electrical potential, e.g., a frequency component which is in the range of approximately 2-7 cycles per minute.

For some applications, receiving the sensor signal includes measuring a change in a physical disposition of a muscle of the subject, or measuring a change in a chemical constituent of the subject.

In a preferred embodiment, receiving the sensor signal includes receiving a signal generated in response to a measurement made at an esophageal site of the subject. Alternatively or additionally, receiving the sensor signal includes receiving a signal generated in response to a measurement made in a vicinity of a stomach of the subject For some applications, receiving the sensor signal includes measuring swallowing of the subject.

In a preferred embodiment, driving the current includes driving a current into aural tissue of the subject.

Typically, driving the current includes driving a current into tissue of a gastrointestinal tract of the subject, e.g., into tissue of a stomach of the subject For example, driving the current may include driving the current into a cardiac site of the stomach, a fundic site of the stomach, a site in a body of the stomach, a distal site of the stomach, a pyloric site of the stomach, and/or an antral site of the stomach. A "cardiac site of the stomach" refers to a site in close proximity to the esophageal opening of the stomach.

For some applications, receiving the sensor signal includes measuring an indication of a quantity of ingesta ingested by the subject, and analyzing the sensor signal includes analyzing the sensor signal responsive to the quantity.

Alternatively or additionally, analyzing the sensor signal includes analyzing the sensor signal responsive to a time of ingestion. For example, analyzing the sensor signal responsive to the time of ingestion may include determining a level of compliance of the subject with an ingestion schedule. Determining the level of compliance typically includes counting a number of meals consumed by the subject during a designated time period, and/or counting a number of times that the subject swallows food. If appropriate, analyzing the sensor signal may additionally include receiving a modification to the ingestion schedule, and analyzing the sensor signal responsive to the modified ingestion schedule. In this latter case, receiving the modification to the ingestion schedule preferably includes receiving the modification by wireless communication from a source outside of the body of the subject.

Driving the current preferably includes applying an Excitable-Tissue Control (ETC) signal to the tissue, applying a fencing signal to the tissue, and/or applying excitatory pulses to the tissue. In a preferred embodiment, the method includes applying a stimulatory pulse at a site of application of the ETC signal. Alternatively or additionally, the method includes applying a stimulatory pulse to tissue at a site other than a site of application of the ETC signal.

For some applications, applying the ETC signal includes detecting natural gastric electrical activity and applying the ETC signal responsive thereto. For example, detecting the natural gastric electrical activity may include detecting the natural gastric electrical activity at a gastric site, and applying the ETC signal may include applying the ETC signal at the same gastric site. Alternatively or additionally, detecting the natural gastric electrical activity includes detecting at a first site, and applying the ETC signal includes applying the ETC signal at a second site, different from the first site. In this latter case, applying the ETC signal at the second site preferably includes timing the application of the ETC signal at the second site responsive to a distance between the first and second sites.

For some applications, driving the current includes:

driving the current into muscle tissue of the subject; and configuring a parameter of the current such that application of the current to the muscle tissue causes an increase in an aspect of contraction of the muscle tissue.

In this case, driving the current typically includes driving the current into muscle tissue of a stomach of the subject, and configuring the parameter includes configuring the parameter such that application of the current to the stomach muscle tissue causes tissue contraction in a first portion of the stomach, and, in conjunction with the subject eating, stretching of a stretch receptor of the stomach in a second portion of the stomach. Alternatively or additionally, driving the current includes driving the current into muscle tissue of a stomach of the subject, and configuring the parameter includes configuring the parameter such that application of the current to the stomach muscle tissue enhances movement of chyme from a fundus to an antrum of the stomach.

Configuring the parameter typically includes configuring the parameter such that application of the current to the muscle tissue induces a sensation of satiation, discomfort, nausea, and/or vertigo of the subject. Alternatively or additionally, driving the current includes configuring a parameter of the current such that application of the current causes gastric dysrhytmia of the subject. Further alternatively or additionally, driving the current includes configuring a parameter of the current such that application of the current disrupts coupling of gastric mechanical activity and gastric electrical activity of the subject.

There is also provided, in accordance with a preferred embodiment of the present invention, apparatus for treating a subject, including:

at least one sensor, adapted to generate a sensor signal responsive to the subject eating;

a set of one or more electrodes, adapted to be coupled to tissue of the subject; and a control unit, adapted to receive the sensor signal, and to drive a current, responsive to analysis of the signal, through the set of electrodes into the tissue.

Preferably, the sensor includes at least one of the electrodes. Alternatively or additionally, the sensor includes a mechanical sensor or at least one sensing electrode. In a preferred embodiment, the sensor includes two sensing electrodes, adapted to be coupled to respective sites of the tissue, and the control unit is adapted to identify a change in a measure of electrical impedance between two sites of the tissue, and to drive the current responsive to identifying the change. Alternatively or additionally, the control unit is adapted to identify a change in a frequency component of a sensed current flowing through the sensing electrode, and to drive a driving current through the set of electrodes responsive to identifying the change in the frequency component of the sensed current.

In a preferred embodiment, the control unit includes a memory, adapted to store an ingestion schedule, and the control unit is adapted to withhold driving the current when the sensor signal is indicative of the subject eating in accordance with the ingestion schedule.

For some applications, the apparatus includes an operator unit, which is adapted to be placed external to the subject and to transmit a control signal to the control unit, wherein the control unit is adapted to analyze the sensor signal responsive to the control signal and to drive the current responsive to analyzing the sensor signal.

The present invention will be more fully understood from the following detailed description of the preferred embodiments thereof, taken together with the drawings, in which:

BRIEF DESCRIPTION OF THE DRAWINGS

FIGS. 9 and 10 are graphs showing strain and voltage measurements in the stomach of an anesthetized pig, before (FIG. 9) and during (FIG. 10) application of a fencing signal thereto, in accordance with a preferred embodiment of the present invention;

DETAILED DESCRIPTION OF PREFERRED EMBODIMENTS

Figure 1:
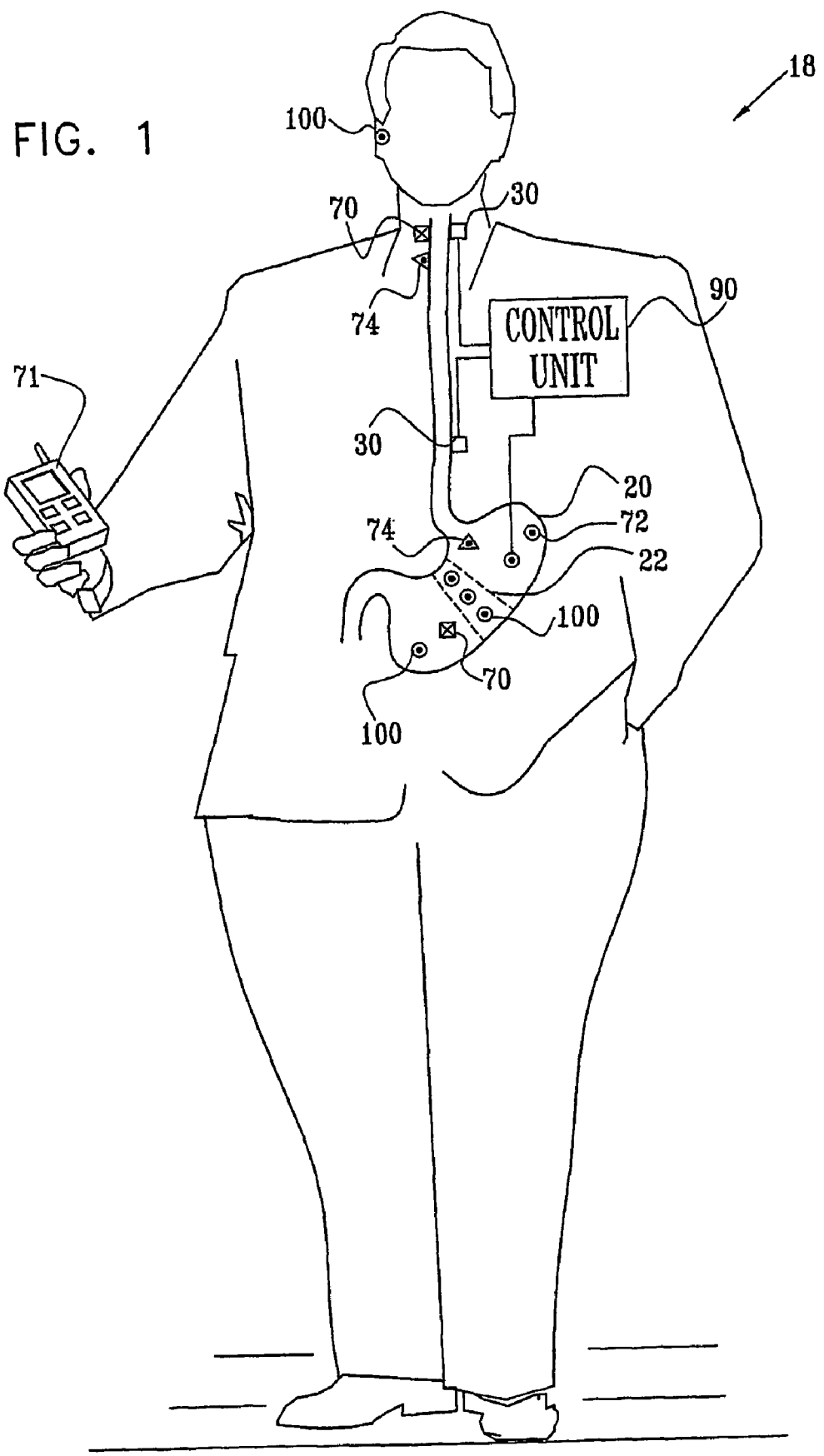
FIG. 1 is a schematic illustration of apparatus for treating obesity, in accordance with a preferred embodiment of the present invention.

FIG. 1 is a schematic illustration of diet regulation apparatus 18, which detects when a patient eats a meal, and determines, based on the detection, whether to apply electrical energy to modify the activity of tissue of the patient, in accordance with a preferred embodiment of the present invention. Apparatus 18 typically comprises mechanical sensors 70, supplemental sensors 72, local sense electrodes 74, operator controls 71, and one or more electrodes 100.

Electrodes 100 are typically coupled to the serosal layer of the stomach and/or inserted into the muscular layer of the stomach. Alternatively or additionally, the electrodes are coupled elsewhere on the stomach, gastrointestinal tract, or to other suitable locations in or on the patient's body. The number of electrodes and sensors, as well as the positions thereof, are shown in FIG. 1 by way of example, and other sites on stomach 20 or in or on the patient's body are appropriate for electrode and sensor placement in other applications of the present invention. Different types of electrodes known in the art are typically selected based on the specific condition of the patient's disorder, and may comprise stitch, coil, screw, patch, basket, needle and/or wire electrodes, or substantially any other electrode known in the art of electrical stimulation or sensing in tissue.

Preferably, apparatus 18 is implanted in the patient in a manner generally similar to that used to implant gastric pacemakers or other apparatus for stimulating the gastrointestinal tract which are known in the art. As appropriate, techniques described in one or more of the patents and patent publications cited in the Background section of the present patent application may be adapted for use with these embodiments of the present invention.

Figure 2:
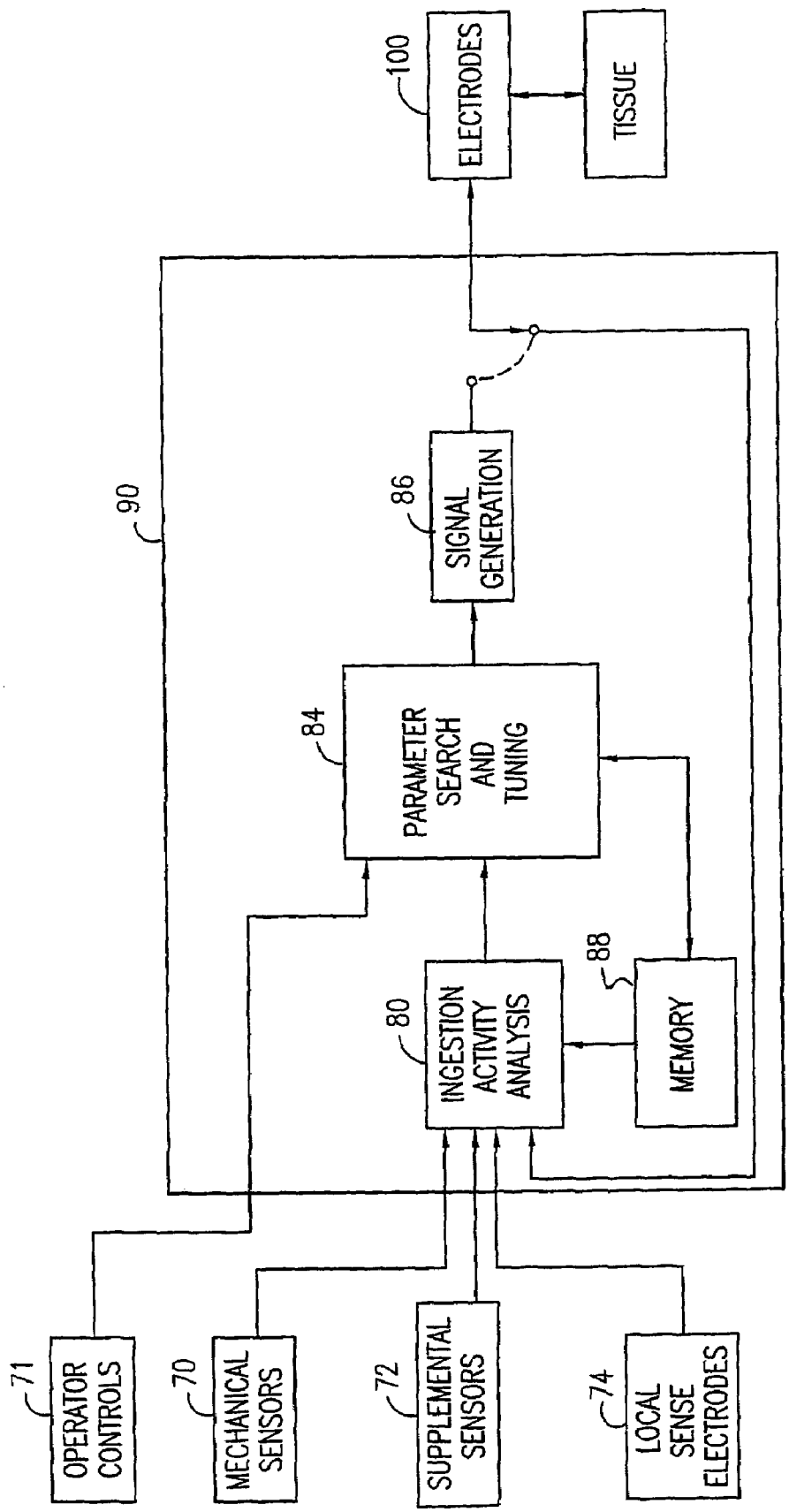
FIG. 2 is a schematic block diagram showing a control unit of the apparatus of FIG. 1, in accordance with a preferred embodiment of the present invention.

FIG. 2 is a schematic block diagram illustrating details of operation of a control unit 90 of apparatus 18, in accordance with a preferred embodiment of the present invention. Preferably, control unit 90 is implanted in the patient, and receives signals from mechanical sensors 70, supplemental sensors 72, and local sense electrodes 74, which are typically implanted on the gastrointestinal tract of the patient or elsewhere on or in the body of the patient. These sensors and electrodes are preferably adapted to provide an "ingestion activity analysis" block 80 of the control unit with information about food ingestion and/or the present state of the stomach.

Preferably, block 80 determines each time that the patient swallows food, or each time that the patient's stomach begins to contract in response to a threshold level of ingested food. For example, local sense electrodes 74 may send signals indicative of contraction of the esophagus or of the stomach, such that block 80 may process the signals to determine whether eating has occurred. Alternatively or additionally, block 80 may filter and process the output of mechanical sensors 70 situated in the esophagus or in the stomach, so as to identify mechanical activity of the gastrointestinal tract indicative of eating. Further alternatively or additionally, block 80 may process data from supplemental sensors 72 concerning the blood sugar level of the patient, to enable an evaluation of whether food has been ingested. (It is to be understood in the context of the present patent application and in the claims that the terms "food" and "eating" apply equally to "liquids" and "drinking.")

Block 80 typically conveys results of its analysis of the inputs from mechanical sensors 70, supplemental sensors 72, and local sense electrodes 74, to a "parameter search and tuning" block 84 of control unit 90. Block 84 preferably evaluates the analysis performed by block 80 with respect to a pre-programmed or variable ingestion schedule stored in a memory block 88 of control unit 90, so as to determine whether the patient is in compliance with the schedule. If it is determined that the patient's eating is not in compliance with the schedule (e.g., the patient has eaten too much at one meal, or has eaten too many meals in a day), then block 84 preferably actuates a signal generator block 86 to generate electrical signals that are applied by electrodes 100 to tissue of the patient. Block 86 preferably comprises amplifiers, isolation units, and other standard circuitry known in the art of electrical signal generation.

The signals generated by block 86 are preferably configured so as to induce a response appropriate for controlling the patient's eating habits. For example, block 86 may drive electrodes 100 to apply signals to the stomach which induce gastric dysrhythmia and the resultant feeling of discomfort or nausea. Alternatively or additionally, the signals are applied to an aural site of the patient (e.g., in a vicinity of the cochlear nerve or the tympanic membrane), and are configured to induce vertigo, or another unpleasant balance-related sensation.

For some applications, control unit 90 drives electrodes 100 to apply a modulation signal to muscle in one area of stomach 20, so as to induce a contraction and/or enhance a spontaneous contraction of the stimulated muscle which, in turn induces satiety, e.g., when food in an adjacent area of the stomach causes additional stretching and/or "pinching" (local, high-intensity contraction) of stretch-receptors therein. This signal may be applied in addition to or instead of the signals described hereinabove which produce gastric or other discomfort. The form of contraction-mediated stretching utilized in these applications simulates the normal appetite-reduction action of the stomach's stretch-receptors, without the patient having eaten the quantities of food which would normally be required to trigger tis appetite-reduction response.

Preferably, the signals applied by electrodes 100 include, as appropriate, an Excitable-Tissue Control (ETC) signal and/or an excitatory signal and/or a fencing signal, so as to induce, modulate, enhance, or inhibit contraction of muscles of the stomach. Aspects of ETC signal application are typically performed in accordance with techniques described in the above-referenced PCT Publications WO 99/03533 and WO 97/25098 and their corresponding U.S. national phase application Ser. Nos. 09/481,253 and 09/101,723, mutatis mutandis. It is noted that for many applications, it is advantageous to apply the various types of signals to the stomach in combination, e.g., to apply an ETC signal and pacing pulses intermittently at the same site, or to apply an ETC signal, an excitatory signal, and a fencing signal at different sites of the stomach, in order to induce sensations which are not conducive to further eating. Alternatively or additionally, an ETC signal may be applied to a site on the stomach shortly after an artificial stimulatory (e.g., pacing) pulse is applied at or near the site, and not in response to detected natural gastric electrical activity.

Preferably, regulation apparatus 18 includes remote operator controls 71, external to the patient's body. This remote unit is typically configured to enable the patient or his physician to change parameters of the ingestion schedule stored in memory block 88. For example, if the patient has lost weight, the physician may change the ingestion schedule to allow a single mid-afternoon snack Alternatively or additionally, operator controls 71 comprise an override button, so that the patient may eat outside of the designated meal times, if the need arises. Operator controls 71 preferably communicate with control unit 90 using standard methods known in the art, such as magnetic induction or radio frequency signals.

Figure 3:
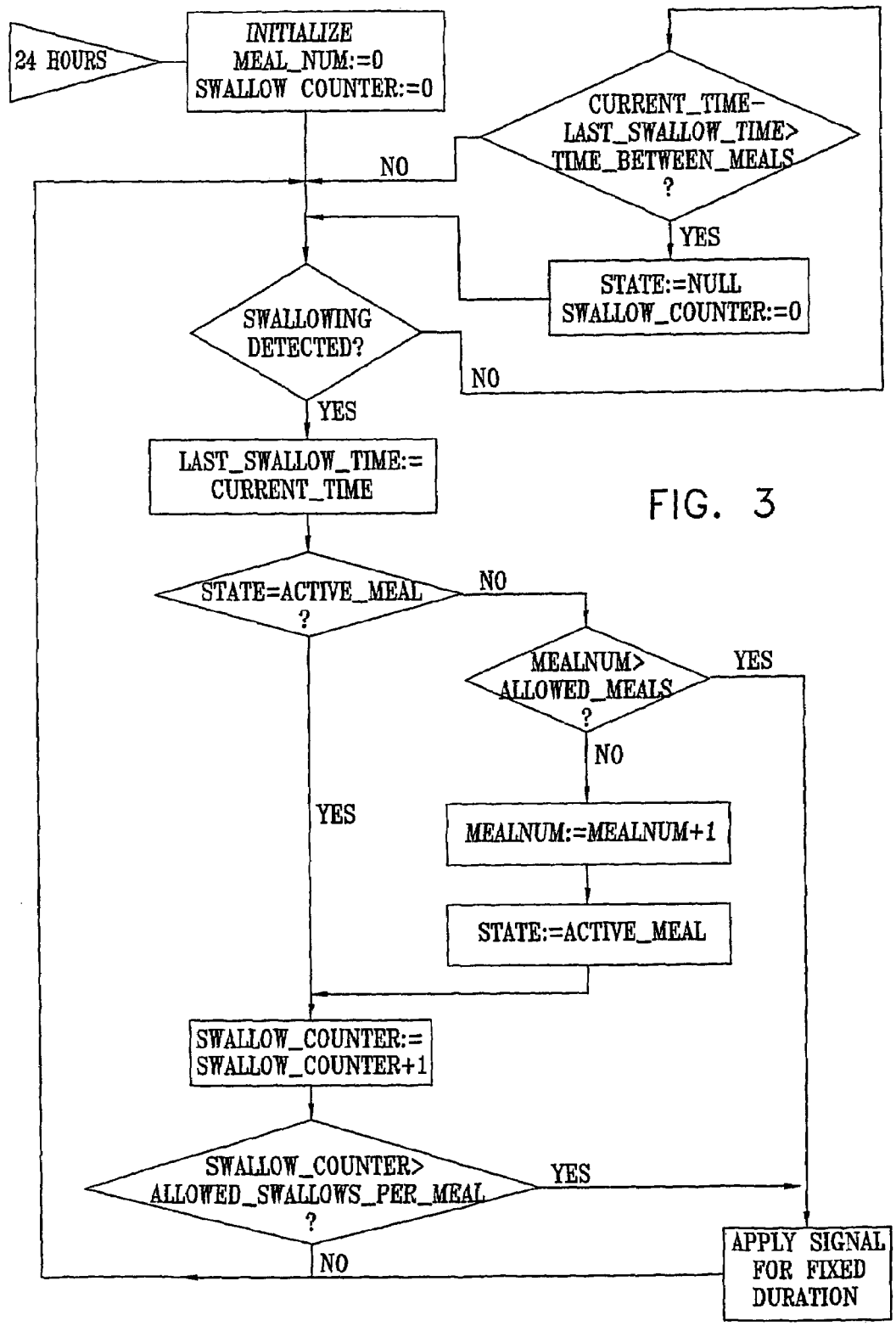
FIG. 3 is a flow chart showing an algorithm for controlling the apparatus of FIG. 1, in accordance with a preferred embodiment of the present invention.

FIG. 3 shows a sample algorithm for controlling apparatus 18, in accordance with a preferred embodiment of the present invention. In this algorithm, the criteria for deciding when to apply the signal which causes the patient discomfort or nausea are based on detecting when the patient swallows food. It will be understood by one skilled in the art, having read the disclosure of the present patent application, however, that other suitable techniques may similarly be applied in order to determine patient compliance with an ingestion schedule. For example, detecting swallowing may be replaced or supplemented by detecting changes in gastric electrical or mechanical activity.

Pre-programmed parameters utilized by control unit 90 in this illustration include the number of allowed meals per day, the number of swallows that define a meal, and the minimum time duration between meals. The steps in the algorithm are seen to be configured such that if either: (a) the number of swallows per meal exceeds that permitted by the pre-programmed schedule, or (b) the number of meals eaten during a day exceeds the allowed number, then a signal will be applied for a fixed duration to electrodes 100, as described hereinabove. It is noted that in addition to the function described above, the variable "time_between_meals" can be set to a relatively low value, e.g., 30 minutes, and thereby allow the patient to swallow food less frequently than once every 30 minutes without having this increase the swallow_counter variable.

It is to be appreciated that whereas the algorithm shown in FIG. 3 places emphasis on monitoring patient swallows, this is by way of illustration and not limitation. For other applications, swallowing is not monitored, or is only monitored as an adjunct to electrical, mechanical, or chemical monitoring performed by sensors in or on the patient's stomach, or elsewhere in or on the patient's body. In a preferred embodiment, the onset of eating or drinking is detected only by monitoring electrical changes (e.g., electrical impedance changes) via electrodes implanted in or on the patient's stomach.

Figure 4A:
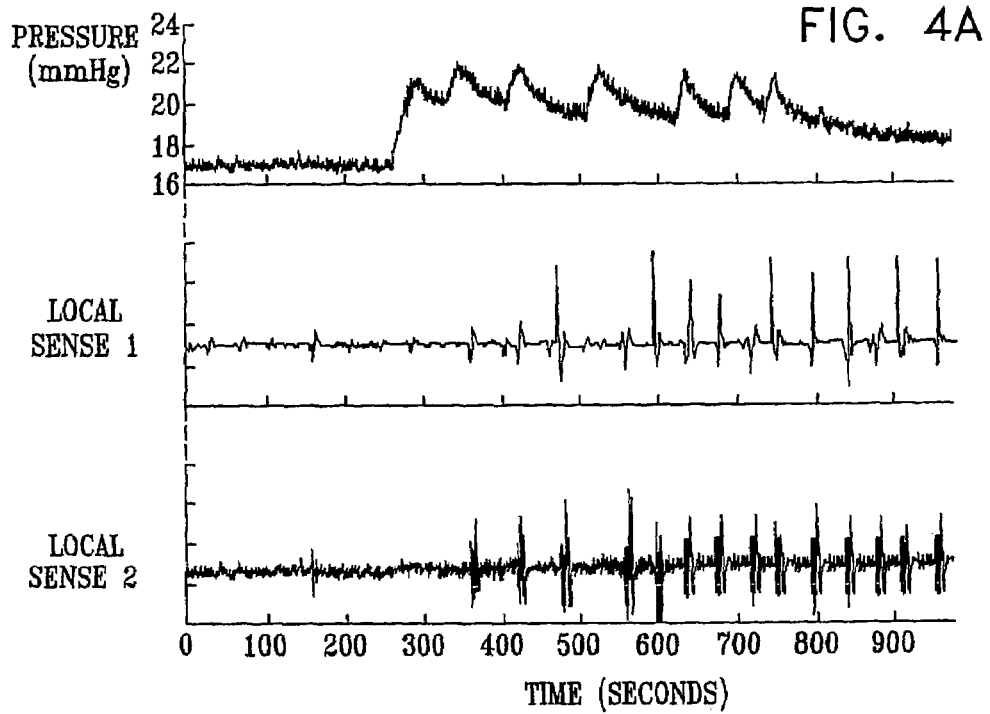
FIG. 4A is a graph showing electrical activity of the stomach of a pig, in response to an imposed intra-gastric pressure change.
Figure 4B:
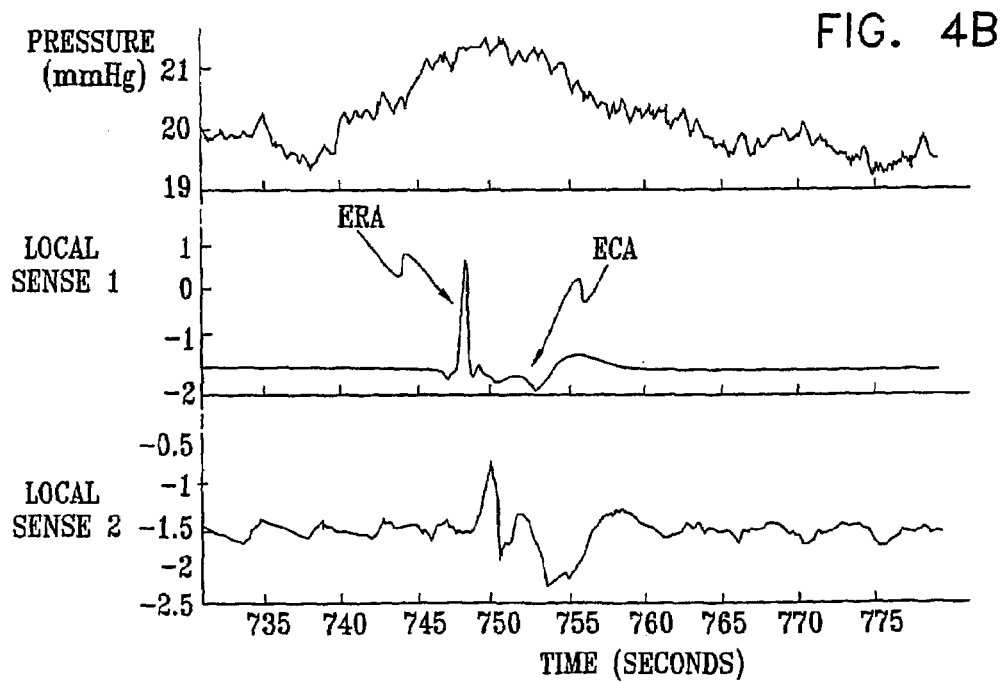
FIG. 4B is a graph illustrating details of the electrical activity shown in FIG. 4A.

Reference is now made to FIGS. 4A and 4B, which are graphs showing the results of an experiment in which a balloon catheter introduced into the stomach of a pig was inflated so as to increase intra-gastric pressure, while the electrical activity of the stomach was continuously measured. FIG. 4B shows a portion of the data from FIG. 4A, magnified along the time axis.

In this experiment, baseline pressure data were recorded by a transducer within the balloon, and gastric electrical activity was simultaneously monitored by sense electrodes placed at two sites on the stomach. During this baseline period, the stomach is seen to be relatively quiet, with Electrical Control Activity (ECA) being present, but without any Electrical Response Activity (ERA). After about 4 minutes, the balloon was inflated, thereby inducing a series of gastric contractions, which are detectable directly in the upper graph of FIG. 4A (pressure), as well as by the frequent ERA seen in the two lower graphs. These results show that changes in electrical activity of the stomach in response to changes in intra-gastric pressure are measurable. In particular, it is seen that the change in intra-gastric pressure of a few mmHg results in a significant morphological change in the measured electrical activity, which can be detected automatically using signal processing techniques known in the art. Preferably, analysis of gastric electrical activity using these techniques is applied to enable automated detection of the changes in intra-gastric pressure resulting from the patient eating.

Figure 5A:
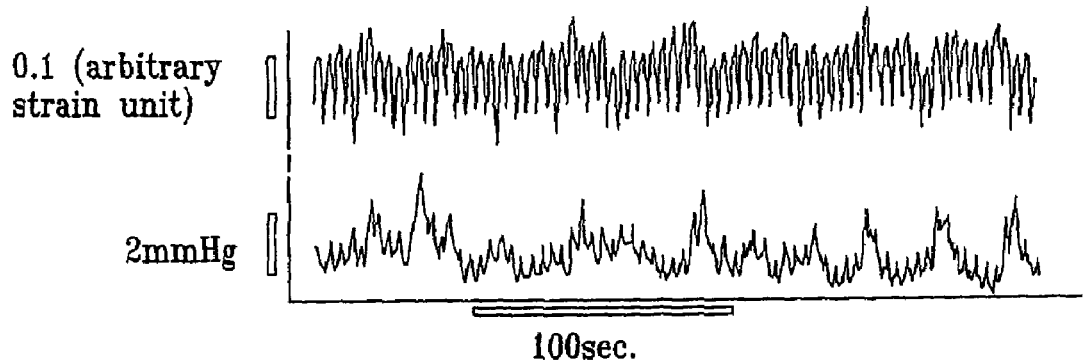
FIG. 5A is a graph showing baseline strain and pressure measurements in the stomach of a pig.
Figure 5B:
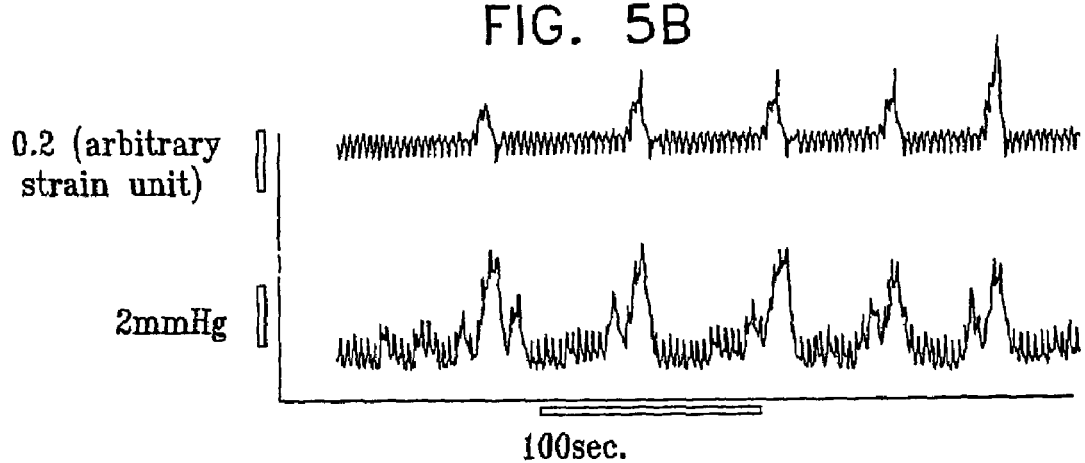
FIG. 5B is a graph showing strain and pressure measurements in the stomach of a pig, in response to application of an Excitable-Tissue Control (ETC) signal thereto, in accordance with a preferred embodiment of the present invention.
Figure 6:
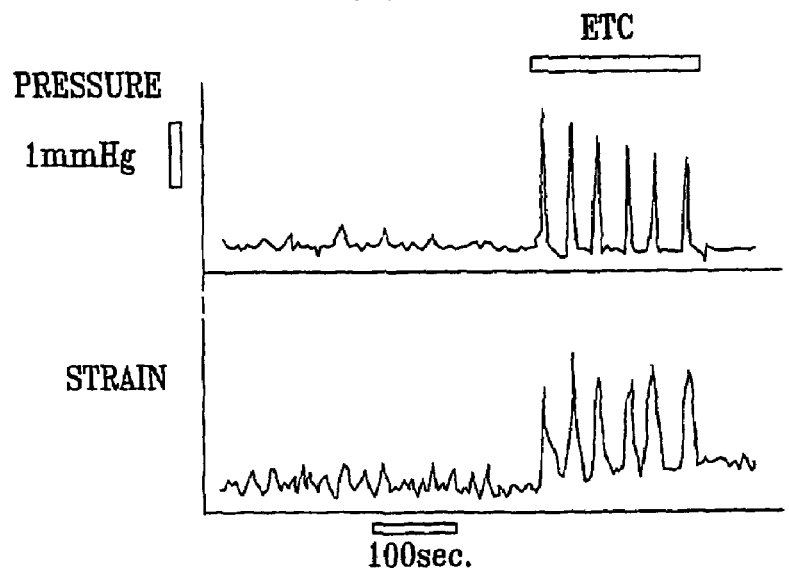
FIG. 6 is a graph showing strain and pressure measurements in a rabbit stomach, in response to application of an ETC signal thereto, in accordance with a preferred embodiment of the present invention.

Reference is now made to FIGS. 5A, 5B, and 6. FIG. 5A is a graph showing experimental baseline strain and pressure measurements in the stomach of a pig. FIG. 5B is a graph showing strain and pressure measurements in the stomach of the same pig, in response to application of an Excitable-Tissue Control (ETC) signal thereto, in accordance with a preferred embodiment of the present invention. FIG. 6 is a graph showing experimental strain and pressure measurements in a rabbit stomach during a baseline period lasting several minutes and during several minutes of ETC signal application, in accordance with a preferred embodiment of the present invention.

The results shown in FIGS. 5B and 6 demonstrate that the application of ETC signals into gastric muscle tissue causes significant increases in wall strain (due to contraction), and corresponding increases in intra-gastric pressure. It is to be understood that application of ETC signals, as part of the ingestion-control signal described hereinabove, is preferred in accordance with some preferred embodiments of the invention. Alternatively or additionally, another signal, e.g., one including pacing pulses or a fencing signal, may be applied so as to induce a sense of patient discomfort or satiety.

Figures 7, 8:
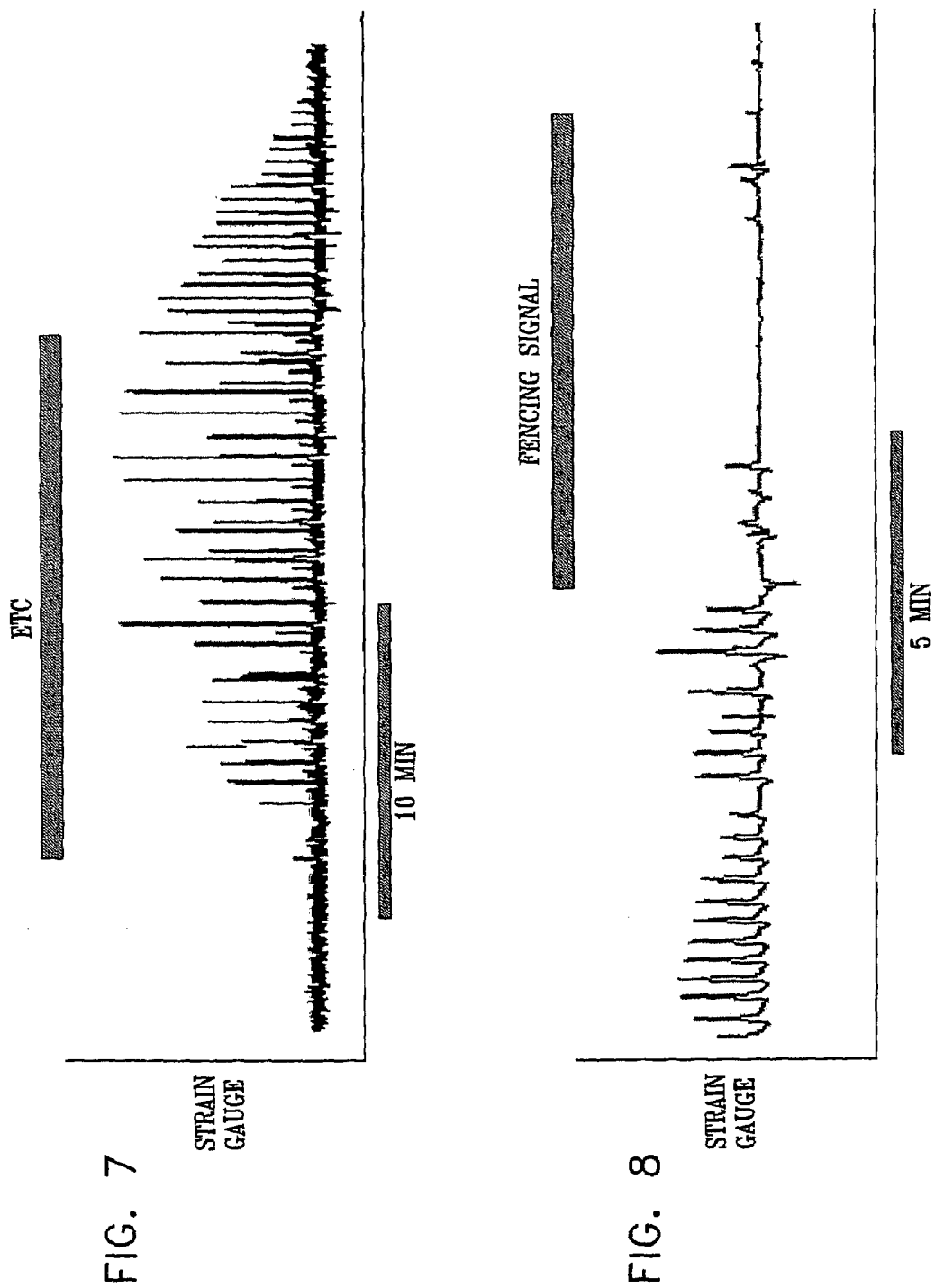
FIG. 7 is a graph showing strain measurements in the stomach of an anesthetized pig, in response to application of an ETC signal thereto, in accordance with a preferred embodiment of the present invention.
FIG. 8 is a graph showing strain measurements in the stomach of an anesthetized pig, in response to application of a fencing signal thereto, in accordance with a preferred embodiment of the present invention.

FIG. 7 is a graph showing strain measurements in a pig stomach, in response to application of an ETC signal thereto, in accordance with a preferred embodiment of the present invention. In this experiment, ETC signals were applied for approximately 16 minutes, during which time it is seen that strain generated by muscles of the stomach increased significantly in response to the ETC signals. Removal of the ETC signals is seen to be associated with a gradual return of the measured values to baseline levels. The ETC signals were applied as a pulse train, immediately following detected gastric electrical activity. In general, a pulse train frequency of approximately 40-120 Hz is believed to be particularly suitable, and in this experiment the frequency was approximately 80 Hz. The duration of ETC pulse trains (or DC signals) is generally optimal if between approximately 500 and 2500 ms, and the duration of the ETC pulse trains in the experiment shown in FIG. 8 was typically approximately 1500 ms. Peak-to-peak ETC signal amplitudes between approximately +/−6 mA and +/−16 mA, typically from +/−8 mA to +/−12 mA were applied to animals in various experiments, including that shown in FIG. 7. Suitable signal amplitude ranges were found to be particular for each animal, and, in clinical use, it is recommended but not required to calibrate the signal amplitude for each patient.

It is noted that two ETC signal protocols have been found particularly useful. In the first, sensing of gastric electrical activity at a site is essentially immediately followed by ETC signal application thereto. In the second protocol, sensing is performed at a proximal (upstream) site, and an ETC signal is applied to a distal (downstream) site at the time when it is estimated that the natural gastric electrical activity sensed at the proximal site will have propagated to the distal site. This time delay is calculated by dividing the distance between the sensing and signal-application electrodes by the estimated propagation velocity of the natural gastric electrical activity. In either protocol, it may be suitable to apply an additional delay, after the gastric electrical activity has initiated at a site, before applying the ETC signal thereto.

FIG. 8 is a graph showing strain measurements in a pig stomach, in response to application of a fencing signal thereto, in accordance with a preferred embodiment of the present invention. Preferred methods and apparatus for applying fencing signals for some applications of the present invention are described in the above-cited PCT Patent Publication WO 98/10830 to Ben-Haim et al., entitled, "Fencing of cardiac muscles," and in U.S. patent application Ser. No. 09/254,903.

In the experiment whose results are shown in FIG. 8 of the present patent application, a DC fencing signal was applied to the stomach between two electrodes placed thereon. During an approximately seven minute signal application period, and for approximately six minutes thereafter, a reduction or modification is seen in mechanical activity. Preferred fencing signal applications parameters include a DC signal having an amplitude of about 0.5 mA-3 mA, and in this experiment the fencing signal was approximately 1 mA. The duration of application of the fencing signal is preferably between about 30 and 90 seconds. It has been observed that it is sometimes advantageous to provide short breaks during the application of the fencing signal, e.g., once every 30 seconds, in order to allow the electrodes to discharge.

It is expected that when analogous stimulation protocols are applied in humans, mutatis mutandis, such a reduction or modification of gastric activity will produce varying levels of discomfort or nausea. It is noted that whereas it is known in the art that when patients experience nausea, there is commonly associated therewith a reduction of gastric electrical activity (particularly a reduction in the rate of slow wave generation), the prior art does not teach the deliberate reduction of gastric activity so as to induce nausea. In other experiments (not shown), it was found that the polarity of the applied fencing signal can be modified so as to affect the response of the muscle tissue.

FIGS. 9 and 10 are graphs showing strain and voltage measurements in a pig stomach, before and during application of a fencing signal thereto, in accordance with a preferred embodiment of the present invention. It is noted that whereas prior to applying the fencing signal the gastric electrical and mechanical activity recorded are coordinated and substantial (FIG. 9), during the fencing signal, the recorded electrical and mechanical activity are reduced essentially to only noise. Advantageously, application of the fencing signal (or another signal) can be used in order to disturb the coupling between the mechanical activity and electrical activity of the stomach, and thereby induce a feeling in the subject which is not conducive to further eating.

Figure 11:
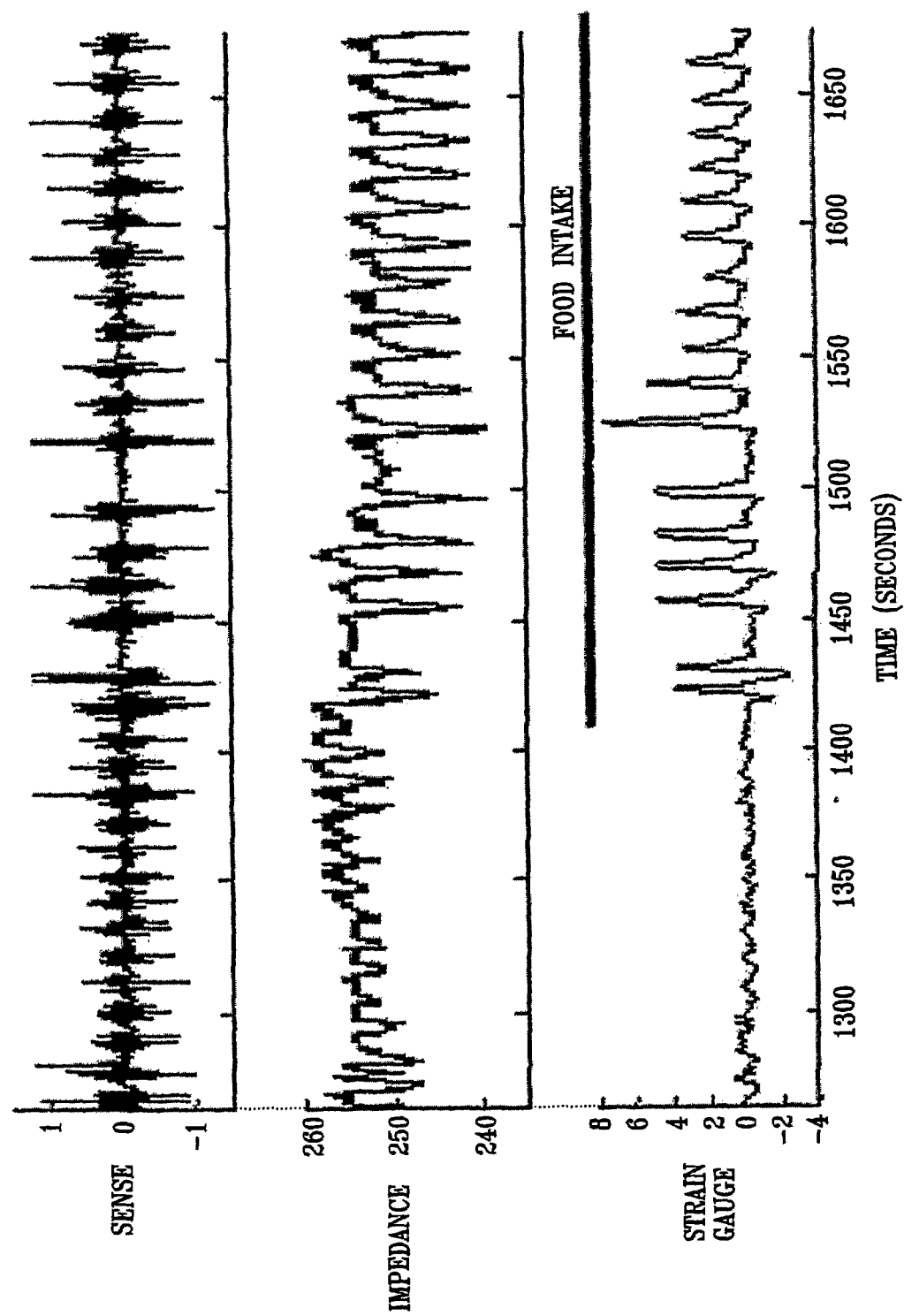
FIG. 11 is a graph showing measurements in the stomach of a dog, prior to and during food intake, measured in accordance with a preferred embodiment of the present invention.

FIG. 11 is a graph showing the correlation between measured electrical and mechanical activity in the antral portion of the stomach of a dog, prior to and during food intake, measured in accordance with a preferred embodiment of the present invention. Impedance measurements were performed using electrodes placed 2-3 cm apart on the stomach, while electrical voltage sensing was performed between two electrodes placed several millimeters apart on the stomach. It is seen that peak-to-peak impedance increases with increasing distension of the stomach, and that some frequency components of the sensed voltage (top graph) and the impedance (middle graph) decrease for at least 15 minutes following the onset of eating.

Figure 12:
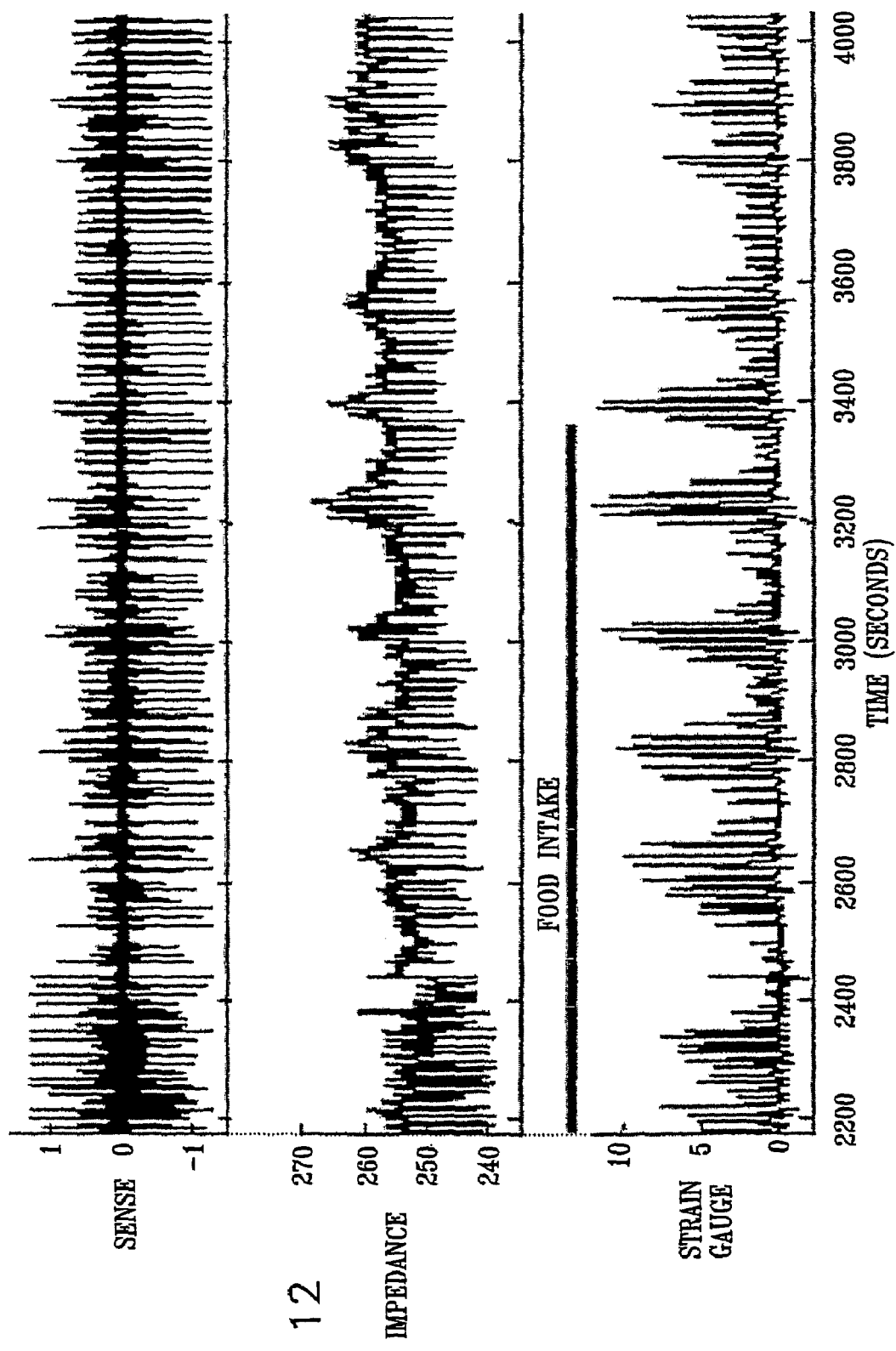
FIG. 12 is a graph showing measurements in the stomach of a dog, during and following food intake, measured in accordance with a preferred embodiment of the present invention.

FIG. 12 is a graph showing measurements made during and following food intake in the stomach of the same animal as in FIG. 11, and shortly after the experiment whose results are shown in FIG. 11, measured in accordance with a preferred embodiment of the present invention. It is noted that gastric mechanical and electrical activity continues, to a smaller extent, and that it can be measured, as is to be expected, even after the discontinuation of food intake at about 3400 seconds.

Figure 13:
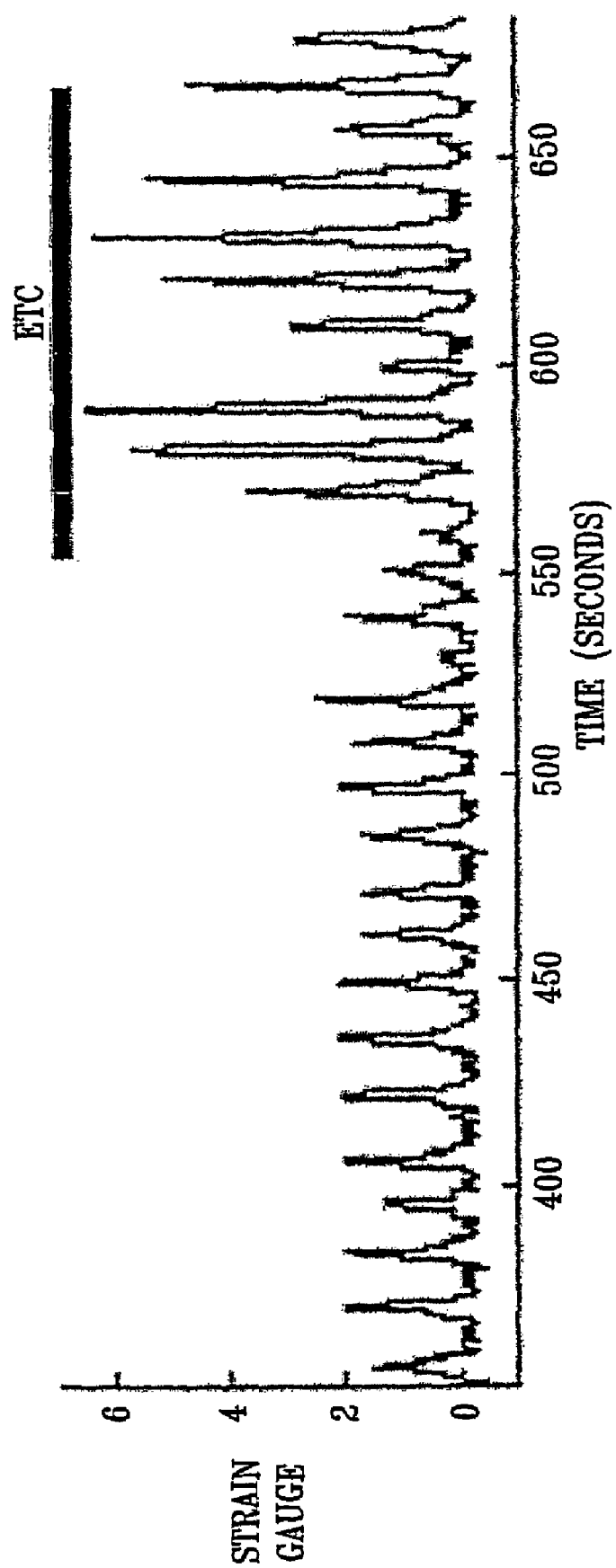
FIG. 13 is a graph showing strain measurements in the stomach of an awake dog, prior to and during application of an ETC signal, in accordance with a preferred embodiment of the present invention.

FIG. 13 is a graph showing strain measurements in the stomach of an awake dog, recorded in accordance with a preferred embodiment of the present invention. The data were obtained following eating, while food was still in the dog's stomach. During the first 200 seconds of the displayed data, regular, relatively low magnitude gastric activity is seen in the strain gauge measurements. At approximately T=550 seconds, an ETC signal was applied, and was configured such that each time an onset of natural electrical activity was detected via one of the sense electrodes (indicating the onset of a contraction), a pulse was administered through the sense electrodes. It is seen that the ETC signal application caused a substantial increase in the magnitude of the measured contractions. For clinical purposes, similar ETC signals may be applied after detecting gastric electric activity.

Figure 14:
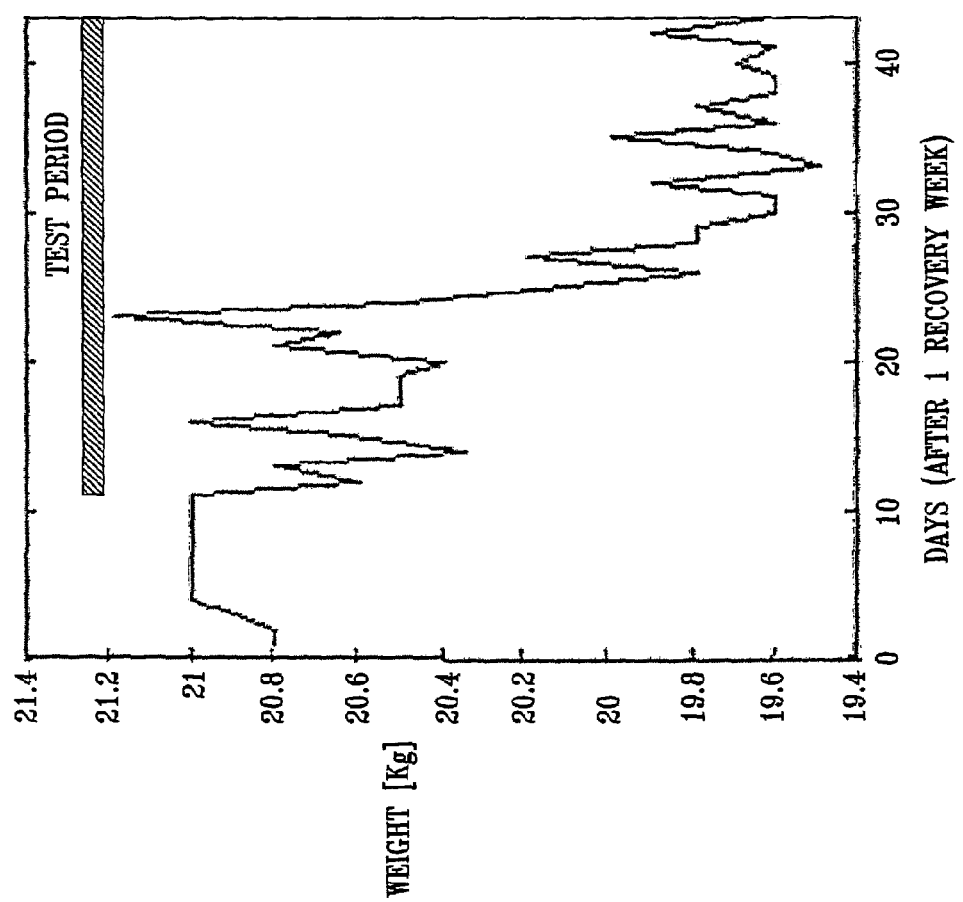
FIG. 14 is a graph showing changes in the weight of a dog during a ten-week experimental period, in accordance with a preferred embodiment of the present invention.

FIG. 14 is a graph showing changes in the weight of a dog during a seven-week experimental period, which was initiated one week after the implantation of electrodes on the dog's stomach, as described hereinabove, in accordance with a preferred embodiment of the present invention. Throughout the experiment, the dog was free to eat ad libitum. Daily weight measurements were performed, and the results prior to and during a test period are shown. During an initial 10 day control period, the dog's weight from days 4-10 is seen to be a stable 21 kg. Thereafter, an ETC signal was applied, and was similar to that applied as described hereinabove with reference to FIG. 7.

The results of this experiment clearly demonstrate that application of ETC as described herein generates a gradual but significant weight loss. In particular, during the 34 days of ETC signal application (from day 11 to day 44), the dog showed a maximal weight loss of 7% (1.5 kg from 21 kg). The dog maintained a generally low weight for two weeks, from day 28 to day 43.

Figure 15:
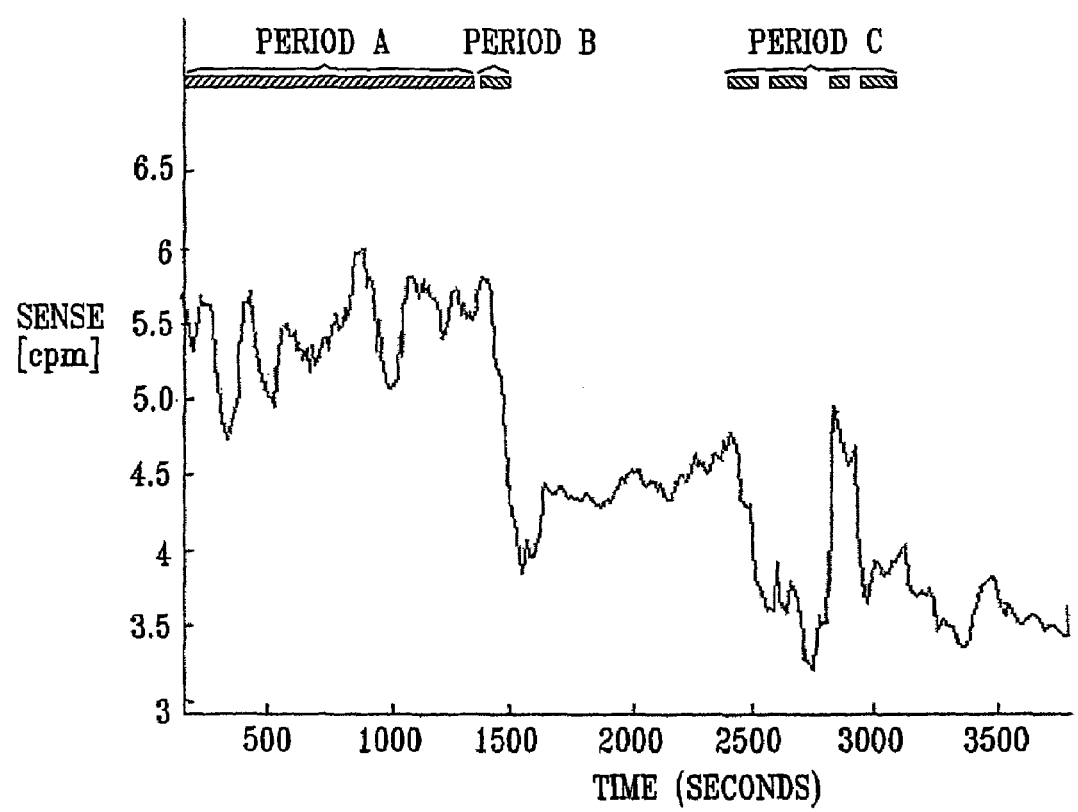
FIG. 15 is a graph showing frequency changes in a recorded electrical signal from the antrum of a dog, in accordance with a preferred embodiment of the present invention.

FIG. 15 is a graph showing calculated frequency changes in an electrical signal recorded from the antrum of a dog during a meal, recorded and analyzed in accordance with a preferred embodiment of the present invention. Three periods are shown, and are based on observations of when the animal was eating. During Period A, eating had not yet commenced, and the frequency of the sensed signal is seen to be generally stable (in the range of 5-6 cycles per minute). During Period B, the animal was fed a measured "pre-load" of 100 grams of food, and this eating is seen to immediately precede a rapid and significant drop in the measured frequency of the electrical signal, which slowly and partially recovered during the following 15 minutes. At this point, the animal was allowed to eat ad libitum, and was seen by observers to eat in four bursts, collectively labeled Period C. The initiation of Period C is characterized, like the initiation of Period B, by a sharp drop in measured signal frequency. During an approximately 3 minute rest period between the second and third burst of Period C, the frequency of the electrical signal was seen again to increase.

It is to be understood that methods and apparatus described hereinabove may be used advantageously in combination with drug treatments or in combination with other therapies designed to treat obesity and/or facilitate greater patient control of eating habits.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method for treating a subject, comprising:
receiving a sensor signal responsive to the subject eating;
analyzing the sensor signal,
wherein receiving the sensor signal comprises sensing, at a gastric site of a stomach of the subject, an electrical potential change generated in association with contraction of muscle of the subject, and
wherein analyzing the sensor signal comprises identifying a decrease in a frequency component of the electrical potential as indicative of the subject eating; and
driving a current into tissue of the stomach responsive to analyzing the signal including identifying the decrease in the frequency component.

2. A method according to claim 1, wherein receiving the sensor signal comprises measuring a change in a physical disposition of a muscle of the subject.

3. A method according to claim 1, and comprising receiving an esophageal signal generated in response to a measurement made at an esophageal site of the subject.

4. A method according to claim 1, wherein driving the current comprises applying a fencing signal to the tissue.

5. A method according to claim 1, wherein driving the current comprises applying excitatory pulses to the tissue.

6. A method according to claim 1, wherein driving the current comprises configuring a parameter of the current such that application of the current causes gastric dysrhythmia of the subject.

7. A method according to claim 1, wherein driving the current comprises configuring a parameter of the current such that application of the current disrupts coupling of gastric mechanical activity and gastric electrical activity of the subject.

8. A method according to claim 1, wherein driving the current comprises configuring a parameter of the current such that application of the current induces a sensation of discomfort in the subject.

9. A method according to claim 1, wherein driving the current comprises configuring a parameter of the current such that application of the current induces a sensation of nausea in the subject.

10. A method according to claim 1, wherein driving the current comprises configuring a parameter of the current such that application of the current induces a sensation of vertigo in the subject.

11. A method according to claim 1, and comprising identifying a change in a measure of electrical impedance between two impedance sensing sites of the stomach.

12. A method according to claim 1, wherein identifying the change comprises identifying a change in a frequency component which is in the range of approximately 2-7 cycles per minute.

13. A method according to claim 1, wherein driving the current comprises driving the current into a cardiac site of the stomach.

14. A method according to claim 1, wherein driving the current comprises driving the current into a fundic site of the stomach.

15. A method according to claim 1, wherein driving the current comprises driving the current into a site in a body of the stomach.

16. A method according to claim 1, wherein driving the current comprises driving the current into a distal site of the stomach.

17. A method according to claim 16, wherein driving the current comprises driving the current into a pyloric site of the stomach.

18. A method according to claim 16, wherein driving the current comprises driving the current into an antral site of the stomach.

19. A method according to claim 1, wherein analyzing the sensor signal comprises analyzing the sensor signal responsive to a time of ingestion.

20. A method according to claim 19, wherein analyzing the sensor signal responsive to the time of ingestion comprises determining a level of compliance of the subject with an ingestion schedule.

21. A method according to claim 20, wherein determining the level of compliance comprises counting a number of meals consumed by the subject during a designated time period.

22. A method according to claim 20, wherein determining the level of compliance comprises counting a number of times that the subject swallows food.

23. A method according to claim 20, wherein analyzing the sensor signal comprises:
receiving a modification to the ingestion schedule; and
analyzing the sensor signal responsive to the modified ingestion schedule.

24. A method according to claim 23, wherein receiving the modification to the ingestion schedule comprises receiving the modification by wireless communication from a source outside of the body of the subject.

25. A method according to claim 1, wherein driving the current comprises applying an Excitable-Tissue Control (ETC) signal to the tissue.

26. A method according to claim 25, and comprising applying a stimulatory pulse at a site of application of the ETC signal.

27. A method according to claim 25, and comprising applying a stimulatory pulse to tissue at a site other than a site of application of the ETC signal.

28. A method according to claim 25, wherein applying the ETC signal comprises detecting natural gastric electrical activity and applying the ETC signal responsive thereto.

29. A method according to claim 28, wherein detecting the natural gastric electrical activity comprises detecting the natural gastric electrical activity at a gastric site, and wherein applying the ETC signal comprises applying the ETC signal at the same gastric site.

30. A method according to claim 28, wherein detecting the natural gastric electrical activity comprises detecting at a first site, and wherein applying the ETC signal comprises applying the ETC signal at a second site, different from the first site.

31. A method according to claim 30, wherein applying the ETC signal at the second site comprises timing the application of the ETC signal at the second site responsive to a distance between the first and second sites.

32. A method according to claim 1, wherein driving the current comprises:
driving the current into muscle tissue of the subject; and
configuring a parameter of the current such that application of the current to the muscle tissue causes an increase in an aspect of contraction of the muscle tissue.

33. A method according to claim 32, wherein driving the current comprises driving the current into muscle tissue of the stomach of the subject, and wherein configuring the parameter comprises configuring the parameter such that application of the current to the stomach muscle tissue causes tissue contraction in a first portion of the stomach, and, in conjunction with the subject eating, stretching of a stretch receptor of the stomach in a second portion of the stomach.

34. A method according to claim 32, wherein driving the current comprises driving the current into muscle tissue of the stomach of the subject, and wherein configuring the parameter comprises configuring the parameter such that application of the current to the stomach muscle tissue enhances movement of chyme from a fundus to an antrum of the stomach.

35. A method according to claim 32, wherein configuring the parameter comprises configuring the parameter such that application of the current to the muscle tissue induces a sensation of satiation of the subject.

36. Apparatus for treating a subject, comprising:
one or more electrodes, which comprise:
a current application set of one or more of the electrodes, adapted to be coupled to current-application tissue of the subject at a site of a stomach of the subject; and
a sensor set of one or more of the electrodes, adapted to be coupled to gastric tissue of the subject at a gastric site of the stomach, and to generate a sensor signal responsive to the subject eating; and
a control unit, adapted to receive the sensor signal, and to drive a current, responsive to analysis of the sensor signal, through the current application set of electrodes into the current-application tissue,
wherein the control unit is adapted to identify a decrease in a frequency component of an electrical potential in a vicinity of the sensor set of electrodes as indicative of the subject eating, and to drive the current through the current application set of electrodes responsive to identifying the decrease in the frequency component of the electrical potential.

37. Apparatus according to claim 36, wherein the current application set and sensor set share at least one of the one or more electrodes.

38. Apparatus according to claim 36, wherein the sensor set is adapted to generate the sensor signal responsive to a quantity of matter ingested by the subject.

39. Apparatus according to claim 36, wherein the sensor set is adapted to generate the sensor signal responsive to a number of meals consumed by the subject.

40. Apparatus according to claim 36, wherein the control unit is adapted to drive the current into the current-application tissue responsive to a time of the subject eating.

41. Apparatus according to claim 36, wherein the control unit is adapted to configure the current such that driving the current induces gastric dysrhythmia.

42. Apparatus according to claim 36, wherein the control unit is adapted to configure the current such that driving the current disrupts coupling of gastric mechanical activity and gastric electrical activity of the subject 43. Apparatus according to claim 36, wherein the control unit is adapted to configure the current such that driving the current induces a sensation of discomfort in the subject.

44. Apparatus according to claim 36, wherein the control unit is adapted to configure the current such that driving the current induces a sensation of nausea in the subject.

45. Apparatus according to claim 36, wherein the control unit is adapted to configure the current such that driving the current induces a sensation of vertigo in the subject.

46. Apparatus according to claim 36, wherein the control unit comprises a memory, adapted to store an ingestion schedule, and wherein the control unit is adapted to withhold driving the current when the sensor signal is indicative of the subject eating in accordance with the ingestion schedule.

47. Apparatus according to claim 36, wherein the current application set is adapted to be placed at a cardiac site of the stomach.

48. Apparatus according to claim 36, wherein the current application set is adapted to be placed at a fundic site of the stomach.

49. Apparatus according to claim 36, wherein the current application set is adapted to be placed at a site on a body of the stomach.

50. Apparatus according to claim 36, wherein the current application set is adapted to be placed at a distal site of the stomach.

51. Apparatus according to claim 50, wherein the current application set is adapted to be placed at a pyloric site of the stomach.

52. Apparatus according to claim 50, wherein the current application set is adapted to be placed at an antral site of the stomach.

53. Apparatus according to claim 36, wherein the one or more electrodes comprise two impedance sensing electrodes, adapted to be coupled to respective impedance sensing sites of the stomach, and wherein the control unit is adapted to identify a change in a measure of electrical impedance between the impedance sensing sites, and to drive the current responsive to identifying the change in the measure of electrical impedance.

54. Apparatus according to claim 36, wherein the control unit is adapted to identify the change in a frequency component that is in the range of approximately 2-7 cycles per minute.

55. Apparatus according to claim 36, wherein the control unit is adapted to drive the current application set to apply an Excitable-Tissue Control (ETC) signal to the current-application tissue.

56. Apparatus according to claim 55, wherein the control unit is adapted to drive the current application set to apply a stitnulatory pulse at a site of application of the ETC signal.

57. Apparatus according to claim 55, wherein the control unit is adapted to drive the current application set to apply a stimulatory pulse to tissue at a site other than a site of application of the ETC signal.

58. Apparatus according to claim 55, wherein the sensor set is adapted to generate the sensor signal responsive to natural gastric electrical activity, and wherein the control unit is adapted to drive the current application set to apply the ETC signal responsive thereto.

59. Apparatus according to claim 58, wherein the sensor set is adapted to generate the sensor signal responsive to natural gastric electrical activity at a site, and wherein the control unit is adapted to drive the current application set to apply the ETC signal at the same site.

60. Apparatus according to claim 58, wherein the sensor set is adapted to generate the sensor signal responsive to natural gastric electrical activity at a first site, and wherein the control unit is adapted to drive the current application set to apply the ETC signal at a second site, different from the first site.

61. Apparatus according to claim 60, wherein the control unit is adapted to time application of the ETC signal responsive to a distance between the first and second sites.

62. Apparatus according to claim 55, wherein the control unit is adapted to drive the current application set to apply the ETC signal in a manner that increases an aspect of contraction of the current-application tissue.

63. Apparatus according to claim 62, wherein the control unit is adapted to drive the current application set to apply the ETC signal in a manner that causes tissue contraction in a first portion of the stomach of the subject, and stretching of a stretch receptor of the stomach in a second portion of the stomach.

64. Apparatus according to claim 55, wherein the control unit is adapted to drive the current application set to apply the ETC signal in a manner that increases a contraction strength of tissue in a vicinity of a stretch receptor of the stomach of the subject and increases a sensation of satiation of the subject.

65. Apparatus according to claim 55, wherein the control unit is adapted to drive the electrode set to apply the ETC signal to the current-application tissue in a manner that enhances movement of chyme from a fundus to an antrum of the stomach of the subject.

66. Apparatus according to claim 36, and comprising an operator unit, which is adapted to be placed external to the subject and to transmit a control signal to the control unit, wherein the control unit is adapted to analyze the sensor signal responsive to the control signal and to drive the current responsive to analyzing the sensor signal.

67. Apparatus according to claim 66, wherein the control unit is adapted to withhold driving the current responsive to the control signal.

68. Apparatus according to claim 66, wherein the control unit is adapted to increase a level of the current responsive to the control signal.

69. Apparatus according to claim 66, wherein the operator unit is adapted to transmit the control signal using wireless communication.

70. A method according to claim 1, wherein the gastric site includes an antral site of the stomach, and wherein sensing comprises sensing at the antral site.

71. A method according to claim 1, wherein the gastric site includes a body site of the stomach, and wherein sensing comprises sensing at the body site.

72. Apparatus according to claim 36, wherein the gastric tissue at the gastric site includes antral tissue at an antral site of the stomach, and wherein the one or more electrodes of the sensor set are adapted to be coupled to the antral tissue at the antral site.

73. Apparatus according to claim 36, wherein the gastric tissue at the gastric site includes body tissue at a body site of the stomach, and wherein the one or more electrodes of the sensor set are adapted to be coupled to the body tissue at the body site.

* * * * *